US011918641B2

(12) United States Patent
Wong et al.

(10) Patent No.: US 11,918,641 B2
(45) Date of Patent: Mar. 5, 2024

(54) CHIMERIC INFLUENZA VACCINES

(71) Applicant: ACADEMIA SINICA, Taipei (TW)

(72) Inventors: Chi-Huey Wong, New Taipei (TW); Hsin-Yu Liao, New Taipel (TW); Shih-Chi Wang, New Taipei (TW); Yi-An Ko, Taipei (TW); Kuo-I Lin, Taipei (TW); Che Ma, New Taipei (TW); Ting-Jen Cheng, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 17/998,208

(22) PCT Filed: May 7, 2021

(86) PCT No.: PCT/US2021/031406
§ 371 (c)(1),
(2) Date: Nov. 8, 2022

(87) PCT Pub. No.: WO2021/226533
PCT Pub. Date: Nov. 11, 2021

(65) Prior Publication Data
US 2023/0302114 A1    Sep. 28, 2023

Related U.S. Application Data

(60) Provisional application No. 63/022,328, filed on May 8, 2020.

(51) Int. Cl.
| A61K 39/145 | (2006.01) |
| A61K 35/76 | (2015.01) |
| A61K 39/00 | (2006.01) |
| A61K 39/12 | (2006.01) |
| A61P 31/16 | (2006.01) |
| C07K 14/005 | (2006.01) |
| C07K 14/11 | (2006.01) |

(52) U.S. Cl.
CPC ............ *A61K 39/145* (2013.01); *A61P 31/16* (2018.01); *C07K 14/005* (2013.01); *A61K 2039/575* (2013.01)

(58) Field of Classification Search
CPC ...... A61K 39/12; A61K 39/145; A61K 35/76; A61P 31/16; C07K 2319/00
See application file for complete search history.

(56) References Cited

U.S. PATENT DOCUMENTS

| 7,871,626 | B2 | 1/2011 | Hoffmann et al. |
| 10,301,377 | B2 | 5/2019 | Graham et al. |
| 10,953,089 | B1 | 3/2021 | Smith et al. |
| 2010/0041740 | A1 | 2/2010 | Wong et al. |
| 2015/0132330 | A1 | 5/2015 | Garcia-Sastre et al. |
| 2016/0199481 | A1 | 7/2016 | Bloom |
| 2018/0043007 | A1 | 2/2018 | LeFebvre et al. |
| 2021/0017563 | A1 | 1/2021 | Bhatnagar et al. |

FOREIGN PATENT DOCUMENTS

| CN | 112626124 | A | 4/2021 |
| EP | 2949665 | A1 | 12/2015 |
| WO | 2007008918 | A2 | 1/2007 |
| WO | 2009002516 | A1 | 12/2008 |
| WO | 2012054907 | A2 | 4/2012 |
| WO | 2012088428 | A1 | 6/2012 |
| WO | 2013043729 | A1 | 3/2013 |
| WO | 2013067652 | A1 | 5/2013 |
| WO | 2015073727 | A1 | 5/2015 |
| WO | 2015184004 | A1 | 12/2015 |
| WO | 2015028478 | A1 | 6/2019 |
| WO | 2019246363 | | 4/2020 |
| WO | 2020172072 | A1 | 8/2020 |
| WO | 2020198865 | A1 | 10/2020 |
| WO | 2021019102 | A2 | 2/2021 |
| WO | 2021045836 | A1 | 3/2021 |
| WO | 2021180602 | A1 | 9/2021 |
| WO | 2021183195 | A1 | 9/2021 |
| WO | 2022221835 | A2 | 10/2022 |
| WO | 2023056482 | A1 | 4/2023 |

OTHER PUBLICATIONS

Castrucci, M.R. et al., "Biologic importance of neuramindase stalk length in influenza A virus", Journal of Virology, 1993, vol. 67, No. 2, pp. 759-764.
Chokhawala, H.A. et al., "Enzymatic Synthesis of Fluorinated Mechanistic Proves for Sialidases and Sialyltransferases", J.Am. Chem. Soc., 2007, p. 10630; scheme 1.
Dowling, W. et al., "Influences of Glycosylation on Antigenicity, Immunogenicity, and Protective Efficacy of Ebola Virus GP DNA Vaccines", J. of Virology, 2007, vol. 81, No. 4, pp. 1821-1837, p. 1822, second column, fourth paragraph; p. 1823, second column, third paragraph; doi:10.1128/JVI.02098-06.
Feng et al., "A Glycolipid Adjuvant, 7DW8-5, Enhances the Protective Immune Response to the Current Slpit Influenza Vaccine in Mice", Frontiers in Microbiology, Sep. 18, 2019, vol. 10, No. 2157M, pp. 1-9; abstract.
Galili, "Amplifying immunogenicity of prospective Covid-19 vaccines by glycoengineering the coronavirus glycan-shield to present alpha-gal epitopes", Vaccine, Aug. 19, 2020; abstract; Fig. 1; DOI: 10.1016/j.vaccine.2020.08032.
GenBank Accession CCH23214, haemagglutinin [Influenza A virus (A/WSN/1933(H1N1))], 2013.

(Continued)

*Primary Examiner* — Barry A Chestnut
(74) *Attorney, Agent, or Firm* — Prosyla Group, PC

(57) ABSTRACT

The present disclosure relates to a chimeric influenza virus hemagglutinin (HA) polypeptide, comprising one or more stem domain sequence, each having at least 60% homology with a stem domain consensus sequence of H1 subtype HA (H1 HA) and/or H5 subtype HA (H5 HA), fused with one or more globular head domain sequence, each having at least 60% homology with a globular head domain consensus sequence of H1 subtype HA (H1 HA) or H5 subtype HA (H5 HA).

14 Claims, 17 Drawing Sheets

Specification includes a Sequence Listing.

(56) References Cited

OTHER PUBLICATIONS

GenBank Accession, ACF54601, neuraminidase [Influenza A virus (A/WSN/1933(H1N1))], 2008.
Gillian, M. Air, "Influenza neuraminidase", Influenza and Other Respiratory Viruses, 2011.
Hayashi, T. et al., "Stereospecific α-Sialylation by Site-Selective Fluorination", Agnew. Chem. Int. Ed., Jan. 25, 2019, vol. 58, pp. 3814-3818. (Whole Document).
Hughes et al., "Adaptation of Influenza A Viruses to Cells Expressing Low Levels of Sialic Acid Leads to Loss of Neuraminidase Activity", Journal of Virology, 2001, vol. 75, No. 8, pp. 3766-3770.
Li, et al., Glycosylation of Neuraminidase Determines the Neurovirulence of Influenza A/WSN/33 Virus, 1993, Journal of Virology, vol. 67, No. 11, pp. 6667-6673.
Liu, Wen-Chun et al., "Unmasking Stem-Specific Neutralizing Epitopes by Abolishing N-Linked Glycosylation Sites of Influenza Virus Hemagglutinin Proteins for Vaccine Design", Journal of Virology, vol. 90 No. 19, Oct. 2016.
Lo, H.-J. et al., "Synthesis of Sialidase-Resistant Oligosaccharide and Antibody Glycoform Containing α2,6-Linked 3Fax-Neu5Ac", J. Am. Chem. Soc., Apr. 10, 2019, vol. 141, No. 16, pp. 6484-6488. (Whole Document.).
Medina, Rafael A. et al., "Glycosylations in the globular head of the hemagglutinin protein modulate the virulence and antigenic properties of the H1N1 influenza viruses", Sci Transl Med., May 29, 2013.
Nobusawa et al., "Comparison of Complete Amino Acid Sequences and Receptor-Binding Properties among 13 Serotypes of Hemagglutinins of Influenza A Viruses", Virology, 182, 475-485 (1991).
Okamoto, K. et al., "An effective synthesis of a-glycosides of N-acetylneuraminic acid by use of 2β-halo-3β-hydroxy-4,7,8,9-tetra-O-acetyl-N-acetylneuraminic acid methyl ester", Tetrahedron Letters, 1986, vol. 27, No. 43, pp. 5233-5236.
Rahman, M Shaminur et al., "Epitope-based chimeric peptide vaccine design against S, M, and E proteins of SARS-CoV-2, the etiologic agent of COVID-19 pandemic, an in silico approach", PeerJ, Jul. 27, 2020 (publication date), DOI 10.7717/peerj.9572, Internal pp. 1-30, Supplemental Information pp. 1, 2. Abstract; and supplemental information pp. 1, 2.
Roberts, Paul C. et al., "Role of Conserved Glycosylation Sites in Maturation and Transport of Influenza A Virus Hemagglutinin", Journal of Virology, Jun. 1993, p. 3048-3060.
Sun et al., "N-Linked Glycosylation of the Hemagglutinin Protein Influences Virulence and Antigenicity of the 1918 Pandemic and Seasonal H1N1 Influenza A Viruses", 2013, Journal of Virology, vol. 87, No. 15, pp. 8756-8766.
Wu, Chung-Yi et al., "Influenza A surface glycosylation and vaccine design", PNAS, Jan. 2017, (Epub Dec. 27, 2016), vol. 114, No. 2, pp. 280-285.
Yang, Zhiwei et al., "Mutation effects of neuraminidases and their docking with ligands: a molecular dynamics and free energy calculation study", J Comput Aided Mol Des, 27: 935-950, 2013.
Zaraket, Hassan et al., "Full Genome Characterization of Human Influenza A/H3N2 Isolates from Asian Countries Reveals a Rare Amantadine Resistance-Conferring Mutation and Novel PB1-F2 Polymorphisms", Frontiers in Microbiology, vol. 7, Article 262, Mar. 2016.
Zhang, Xiaojian et al., "Role of stem glycans attached haemagglutinin in the biological characteristics of H5N1 avian influenza virus", Journal of General Virology, 96, 1248-1257, 2015.
Zhang, Yan et al., "Glycosylation on Hemagglutinin Affects the Virulence and Pathogenicity of Pandemic H1N1/2009 Influenza A Virus in Mice", PLOS ONE, vol. 8, Issue 4, Apr. 2013.
Zhao, "Glycans of SARS-CoV-2 Spike Protein in Virus Infection and Antibody Production", Frontiers in Molecular Biosciences, Apr. 13, 2021; Entire Document; DOI: 10.3389/fmolb.2021.629873.
Zheng, J. et al., "Identification of N-linked glycosylation sites in the spike protein and their functional impact on the replication and infectivity of coronavirus infectious bronchitis virus in cell culture", Virology, Oct. 13, 2017, vol. 513, pp. 65-74; abstract; p. 65, 1st column, second paragraph; p. 66, column, 5th paragraph; p. 68, first column, first, third paragraphs; Table 3; figure 5; http://dx.doi.org/10.1016/j.virol.2017.10.003.
U.S. Appl. No. 17/598,064, filed Sep. 24, 2021, Chi-Huey Wong.
U.S. Appl. No. 17/937,744, filed Oct. 3, 2022, Kuo-I Lin.
U.S. Appl. No. 18/005,573, filed Jan. 13, 2023, Che Ma.
U.S. Appl. No. 18/146,873, file Dec. 27, 2022, Kuo-I Lin.
Cao, Yiwei et al., "Dynamic Interactions of Fully Glycosylated SARS-CoV-2 Spike Protein with Various Antibodies," JCTC, Sep. 16, 2021, vol. 17, pp. 6559-6569.
Edwards, et al., "The Remarkable Flexibility of the Human Antibody Repertoire; Isolation of Over One Thousand Different Antibodies to a Single Protein, BLyS," J. Mol. Biol., Nov. 2003, 14:334(1): 10-18; doi: 10.1016/jmb.2003.09.054. PMID 14596803.
Goel, Manisha et al., "Plasticity within the Antigen-Combining Site May Manifest as Molecular Mimicry in the Humoral Immune Response," J. Immunol., Dec. 15, 2004, 173(12):7358-67 PMID: 15585860 DOI: 10.4049/jimmunol.173.12.7358.
Janeway Jr., Charles A et al., "Immunobiology: The Immune System in Health and Disease," 3rd edition, Garland Publishing Inc., 1997, pp. 3:1-3:11.
Kanyavuz, Alexia et al., "Breaking the law: unconventional strategies for antibody diversification," Nat Rev Immunol., Jun. 2019, 19(6):355-368. doi:10.1038/S41577-019-0126-7. PMID: 30718829.
Lescar et al., "Crystal Structure of a Cross-reaction Complex between Fab F9.13.7 and Guinea Fowl Lysozyme," J Biol Chem., Jul. 1995, 270(30):18067-76. doi: 10.1074/jbc.270.30.18067. PMID: 7629116.
Lloyd, C. et al., "Modelling the human immune response: performance of a 10(11) human antibody repertoire against a broad panel of therapeutically relevant antigens," Protein Engineering Design & Selection, 2009, vol. 22, No. 3, pp. 159-168. doi: 10.1093/protein/gzn058.
Non-Final Office Action issued in U.S. Appl. No. 17/937,744 dated Jul. 5, 2023.
Rees-Spear, Chloe et al., "The effect of spike mutations on SARS-CoV-2 neutralization," Cell Rep., Mar. 2023, 34 (12): 108890. Published online Mar. 6, 2021. doi: 10.1016/j.celrep.2021.108890: 10.1016/j.celrep.2021.108890 PMCID: PMC7936541 PMID: 33713594.
Rudikoff et al., "Single amino acid substitution altering antigen-binding specificity," Proc. Natl Acad Sci U S A, Mar. 1982, vol. 79(6), pp. 1979-1983. doi: 10.1073/pnas.79.6.1979. PC/D: 6804-947.

A Secreted HA constructs

| signal peptide | HA1 | | cleavage site | HA2 | thrombin cleavage site | foldon 6xHis |
| 1 17 | C52 | C277 | 344 | 520 | 567 | globular head domain

Stem region

Fig. 6

```
                       SEQUENCE LISTING

<160> NUMBER OF SEQ ID NOS: 14

<210> SEQ ID NO 1
    <211> LENGTH: 41
    <212> TYPE: PRT
    <213> ORGANISM: Influenza A virus

<400> SEQUENCE: 1

Asp Thr Leu Cys Ile Gly Tyr His Ala Asn Asn Ser Thr Asp Thr Val
    1               5                   10                  15

Asp Thr Val Leu Glu Lys Asn Val Thr Val Thr His Ser Val Asn Leu
                    20                  25                  30

Leu Glu Asp Lys His Asn Gly Lys Leu
                35                  40

<210> SEQ ID NO 2
    <211> LENGTH: 237
    <212> TYPE: PRT
    <213> ORGANISM: Influenza A virus

<400> SEQUENCE: 2

Asn Thr Thr Cys Gln Thr Pro Lys Gly Ala Ile Asn Thr Ser Leu Pro
    1               5                   10                  15

Phe Gln Asn Ile His Pro Ile Thr Ile Gly Lys Cys Pro Lys Tyr Val
                    20                  25                  30

Lys Ser Thr Lys Leu Arg Leu Ala Thr Gly Leu Arg Asn Val Pro Ser
                35                  40                  45

Ile Gln Ser Arg Gly Leu Phe Gly Ala Ile Ala Gly Phe Ile Glu Gly
            50                  55                  60

Gly Trp Thr Gly Met Val Asp Gly Trp Tyr Gly Tyr His His Gln Asn
    65                  70                  75                  80

Glu Gln Gly Ser Gly Tyr Ala Ala Asp Leu Lys Ser Thr Gln Asn Ala
                    85                  90                  95

Ile Asp Lys Ile Thr Asn Lys Val Asn Ser Val Ile Glu Lys Met Asn
                    100                 105                 110

Thr Gln Phe Thr Ala Val Gly Lys Glu Phe Asn His Leu Glu Lys Arg
                115                 120                 125

Ile Glu Asn Leu Asn Lys Lys Val Asp Asp Gly Phe Leu Asp Ile Trp
            130                 135                 140

Thr Tyr Asn Ala Glu Leu Leu Val Leu Leu Glu Asn Glu Arg Thr Leu
    145                 150                 155                 160

Asp Tyr His Asp Ser Asn Val Lys Asn Leu Tyr Glu Lys Val Arg Asn
                    165                 170                 175

Gln Leu Lys Asn Asn Ala Lys Glu Ile Gly Asn Gly Cys Phe Glu Phe
                180                 185                 190

Tyr His Lys Cys Asp Asn Thr Cys Met Glu Ser Val Lys Asn Gly Thr
                195                 200                 205
```

```
Tyr Asp Tyr Pro Lys Tyr Ser Glu Glu Ala Lys Leu Asn Arg Glu Glu
            210                 215                 220

Ile Asp Gly Val Lys Leu Glu Ser Thr Arg Ile Tyr Gln
225                 230                 235

<210> SEQ ID NO 3
<211> LENGTH: 233
<212> TYPE: PRT
<213> ORGANISM: Influenza A virus

<400> SEQUENCE: 3

Cys Asp Leu Asp Gly Val Lys Pro Leu Ile Leu Arg Asp Cys Ser Val
1               5                   10                  15

Ala Gly Trp Leu Leu Gly Asn Pro Met Cys Asp Glu Phe Ile Asn Val
            20                  25                  30

Pro Glu Trp Ser Tyr Ile Val Glu Lys Ala Asn Pro Ala Asn Asp Leu
        35                  40                  45

Cys Tyr Pro Gly Asn Phe Asn Asp Tyr Glu Glu Leu Lys His Leu Leu
    50                  55                  60

Ser Arg Ile Asn His Phe Glu Lys Ile Gln Ile Ile Pro Lys Ser Ser
65                  70                  75                  80

Trp Ser Asp His Glu Ala Ser Ser Gly Val Ser Ser Ala Cys Pro Tyr
                85                  90                  95

Gln Gly Lys Ser Ser Phe Phe Arg Asn Val Val Trp Leu Ile Lys Lys
            100                 105                 110

Asn Ser Thr Tyr Pro Thr Ile Lys Arg Ser Tyr Asn Asn Thr Asn Gln
        115                 120                 125

Glu Asp Leu Leu Val Leu Trp Gly Ile His His Pro Asn Asp Ala Ala
    130                 135                 140

Glu Gln Thr Arg Leu Tyr Gln Asn Pro Thr Thr Tyr Ile Ser Val Gly
145                 150                 155                 160

Thr Ser Thr Leu Asn Gln Arg Leu Val Pro Lys Ile Ala Thr Arg Ser
                165                 170                 175

Lys Val Asn Gly Gln Ser Gly Arg Met Glu Phe Phe Trp Thr Ile Leu
            180                 185                 190

Lys Pro Asn Asp Ala Ile Asn Phe Glu Ser Asn Gly Asn Phe Ile Ala
        195                 200                 205

Pro Glu Tyr Ala Tyr Lys Ile Val Lys Lys Gly Asp Ser Thr Ile Met
    210                 215                 220

Lys Ser Glu Leu Glu Tyr Gly Asn Cys
225                 230

<210> SEQ ID NO 4
<211> LENGTH: 511
<212> TYPE: PRT
<213> ORGANISM: Artificial Sequence
<220> FEATURE:
<223> OTHER INFORMATION: chimeric influenza virus HA polypeptide

<400> SEQUENCE: 4

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Asp Leu Asp Gly Val Lys
        35                  40                  45
```

-continued

```
Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Thr Cys Gln Thr Pro Lys Gly Ala Ile Asn Thr Ser
        275                 280                 285

Leu Pro Phe Gln Asn Ile His Pro Ile Thr Ile Gly Lys Cys Pro Lys
    290                 295                 300

Tyr Val Lys Ser Thr Lys Leu Arg Leu Ala Thr Gly Leu Arg Asn Val
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Leu Lys Ser Thr Gln
        355                 360                 365

Asn Ala Ile Asp Lys Ile Thr Asn Lys Val Asn Ser Val Ile Glu Lys
    370                 375                 380

Met Asn Thr Gln Phe Thr Ala Val Gly Lys Glu Phe Asn His Leu Glu
385                 390                 395                 400

Lys Arg Ile Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Tyr His Asp Ser Asn Val Lys Asn Leu Tyr Glu Lys Val
        435                 440                 445

Arg Asn Gln Leu Lys Asn Asn Ala Lys Glu Ile Gly Asn Gly Cys Phe
    450                 455                 460

Glu Phe Tyr His Lys Cys Asp Asn Thr Cys Met Glu Ser Val Lys Asn
```

```
                465                 470                 475                 480
Gly Thr Tyr Asp Tyr Pro Lys Tyr Ser Glu Glu Ala Lys Leu Asn Arg
                    485                 490                 495

Glu Glu Ile Asp Gly Val Lys Leu Glu Ser Thr Arg Ile Tyr Gln
                500                 505                 510

<210> SEQ ID NO 5
<211> LENGTH: 41
<212> TYPE: PRT
<213> ORGANISM: Influenza A virus

<400> SEQUENCE: 5

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Lys His Asn Gly Lys Leu
            35                  40

<210> SEQ ID NO 6
<211> LENGTH: 228
<212> TYPE: PRT
<213> ORGANISM: Artificial Sequence
<220> FEATURE:
<223> OTHER INFORMATION: stem domain consensus sequence of H1 HA and H5
      HA

<400> SEQUENCE: 6

Asn Thr Thr Cys Gln Thr Pro Lys Gly Ala Ile Asn Thr Ser Leu Pro
1               5                   10                  15

Phe Gln Asn Ile His Pro Ile Thr Ile Gly Lys Cys Pro Lys Tyr Val
                20                  25                  30

Lys Ser Thr Lys Leu Arg Leu Ala Thr Gly Leu Arg Asn Val Pro Ser
            35                  40                  45

Ile Gln Ser Arg Gly Leu Phe Gly Ala Ile Ala Gly Phe Ile Glu Gly
        50                  55                  60

Gly Trp Gln Gly Met Val Asp Gly Trp Tyr Gly Tyr His His Ser Asn
65                  70                  75                  80

Glu Gln Gly Ser Gly Tyr Ala Ala Asp Lys Glu Ser Thr Gln Lys Ala
                85                  90                  95

Ile Asp Gly Val Thr Asn Lys Val Asn Ser Ile Ile Asp Lys Met Asn
            100                 105                 110

Thr Gln Phe Glu Ala Val Gly Arg Glu Phe Asn Asn Leu Glu Arg Arg
        115                 120                 125

Ile Glu Asn Leu Asn Lys Lys Met Glu Asp Gly Phe Leu Asp Val Trp
    130                 135                 140

Thr Tyr Asn Ala Glu Leu Leu Val Leu Met Glu Asn Glu Arg Thr Leu
145                 150                 155                 160

Asp Phe His Asp Ser Asn Val Lys Asn Leu Tyr Asp Lys Val Arg Leu
                165                 170                 175

Gln Leu Arg Asp Asn Ala Lys Glu Leu Gly Asn Gly Cys Phe Glu Phe
            180                 185                 190

Tyr His Lys Cys Asp Asn Glu Cys Met Glu Ser Val Arg Asn Gly Thr
        195                 200                 205

Tyr Asp Tyr Pro Gln Tyr Ser Glu Glu Ala Arg Leu Lys Arg Glu Glu
    210                 215                 220

Ile Ser Gly Val
```

<210> SEQ ID NO 7
<211> LENGTH: 234
<212> TYPE: PRT
<213> ORGANISM: Influenza A virus

<400> SEQUENCE: 7

```
Cys Lys Leu Arg Gly Val Ala Pro Leu His Leu Gly Lys Cys Asn Ile
1               5                  10                  15

Ala Gly Trp Ile Leu Gly Asn Pro Glu Cys Glu Ser Leu Ser Thr Ala
            20                  25                  30

Ser Ser Trp Ser Tyr Ile Val Glu Thr Ser Ser Asp Asn Gly Thr
        35                  40                  45

Cys Tyr Pro Gly Asp Phe Ile Asp Tyr Glu Glu Leu Arg Glu Gln Leu
    50                  55                  60

Ser Ser Val Ser Ser Phe Glu Arg Phe Glu Ile Phe Pro Lys Thr Ser
65                  70                  75                  80

Ser Trp Pro Asn His Asp Ser Asn Lys Gly Val Thr Ala Ala Cys Pro
                85                  90                  95

His Ala Gly Ala Lys Ser Phe Tyr Lys Asn Leu Ile Trp Leu Val Lys
            100                 105                 110

Lys Gly Asn Ser Tyr Pro Lys Leu Ser Lys Ser Tyr Ile Asn Asp Lys
        115                 120                 125

Gly Lys Glu Val Leu Val Leu Trp Gly Ile His His Pro Ser Thr Thr
130                 135                 140

Ala Asp Gln Gln Ser Leu Tyr Gln Asn Ala Asp Ala Tyr Val Phe Val
145                 150                 155                 160

Gly Thr Ser Arg Tyr Ser Lys Lys Phe Lys Pro Glu Ile Ala Ile Arg
                165                 170                 175

Pro Lys Val Arg Asp Gln Glu Gly Arg Met Asn Tyr Tyr Trp Thr Leu
            180                 185                 190

Val Glu Pro Gly Asp Lys Ile Thr Phe Glu Ala Thr Gly Asn Leu Val
        195                 200                 205

Val Pro Arg Tyr Ala Phe Ala Met Glu Arg Asn Ala Gly Ser Gly Ile
210                 215                 220

Ile Ile Ser Asp Thr Pro Val His Asp Cys
225                 230
```

<210> SEQ ID NO 8
<211> LENGTH: 503
<212> TYPE: PRT
<213> ORGANISM: Artificial Sequence
<220> FEATURE:
<223> OTHER INFORMATION: chimeric influenza virus HA polypeptide

<400> SEQUENCE: 8

```
Asp Thr Leu Cys Ile G

```
Glu Thr Ser Ser Ser Asp Asn Gly Thr Cys Tyr Pro Gly Asp Phe Ile
                85                  90                  95
Asp Tyr Glu Glu Leu Arg Glu Gln Leu Ser Ser Val Ser Ser Phe Glu
            100                 105                 110
Arg Phe Glu Ile Phe Pro Lys Thr Ser Ser Trp Pro Asn His Asp Ser
        115                 120                 125
Asn Lys Gly Val Thr Ala Ala Cys Pro His Ala Gly Ala Lys Ser Phe
130                 135                 140
Tyr Lys Asn Leu Ile Trp Leu Val Lys Lys Gly Asn Ser Tyr Pro Lys
145                 150                 155                 160
Leu Ser Lys Ser Tyr Ile Asn Asp Lys Gly Lys Glu Val Leu Val Leu
                165                 170                 175
Trp Gly Ile His His Pro Ser Thr Thr Ala Asp Gln Gln Ser Leu Tyr
            180                 185                 190
Gln Asn Ala Asp Ala Tyr Val Phe Val Gly Thr Ser Arg Tyr Ser Lys
        195                 200                 205
Lys Phe Lys Pro Glu Ile Ala Ile Arg Pro Lys Val Arg Asp Gln Glu
        210                 215                 220
Gly Arg Met Asn Tyr Tyr Trp Thr Leu Val Glu Pro Gly Asp Lys Ile
225                 230                 235                 240
Thr Phe Glu Ala Thr Gly Asn Leu Val Val Pro Arg Tyr Ala Phe Ala
                245                 250                 255
Met Glu Arg Asn Ala Gly Ser Gly Ile Ile Ile Ser Asp Thr Pro Val
            260                 265                 270
His Asp Cys Asn Thr Thr Cys Gln Thr Pro Lys Gly Ala Ile Asn Thr
        275                 280                 285
Ser Leu Pro Phe Gln Asn Ile His Pro Ile Thr Ile Gly Lys Cys Pro
290                 295                 300
Lys Tyr Val Lys Ser Thr Lys Leu Arg Leu Ala Thr Gly Leu Arg Asn
305                 310                 315                 320
Val Pro Ser Ile Gln Ser Arg Gly Leu Phe Gly Ala Ile Ala Gly Phe
                325                 330                 335
Ile Glu Gly Gly Trp Gln Gly Met Val Asp Gly Trp Tyr Gly Tyr His
            340                 345                 350
His Ser Asn Glu Gln Gly Ser Gly Tyr Ala Ala Asp Lys Glu Ser Thr
        355                 360                 365
Gln Lys Ala Ile Asp Gly Val Thr Asn Lys Val Asn Ser Ile Ile Asp
        370                 375                 380
Lys Met Asn Thr Gln Phe Glu Ala Val Gly Arg Glu Phe Asn Asn Leu
385                 390                 395                 400
Glu Arg Arg Ile Glu Asn Leu Asn Lys Lys Met Glu Asp Gly Phe Leu
                405                 410                 415
Asp Val Trp Thr Tyr Asn Ala Glu Leu Leu Val Leu Met Glu Asn Glu
            420                 425                 430
Arg Thr Leu Asp Phe His Asp Ser Asn Val Lys Asn Leu Tyr Asp Lys
        435                 440                 445
Val Arg Leu Gln Leu Arg Asp Asn Ala Lys Glu Leu Gly Asn Gly Cys
        450                 455                 460
Phe Glu Phe Tyr His Lys Cys Asp Asn Glu Cys Met Glu Ser Val Arg
465                 470                 475                 480
Asn Gly Thr Tyr Asp Tyr Pro Gln Tyr Ser Glu Glu Ala Arg Leu Lys
                485                 490                 495
```

```
Arg Glu Glu Ile Ser Gly Val
            500

<210> SEQ ID NO 9
<211> LENGTH: 41
<212> TYPE: PRT
<213> ORGANISM: Influenza A virus

<400> SEQUENCE: 9

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu
        35                  40

<210> SEQ ID NO 10
<211> LENGTH: 232
<212> TYPE: PRT
<213> ORGANISM: Artificial Sequence
<220> FEATURE:
<223> OTHER INFORMATION: stem domain consensus sequence of H1 HA and H5
      HA

<400> SEQUENCE: 10

Asn Thr Lys Cys Gln Thr Pro Met Gly Ala Ile Asn Ser Ser Met Pro
1               5                   10                  15

Phe His Asn Ile His Pro Leu Thr Ile Gly Glu Cys Pro Lys Tyr Val
            20                  25                  30

Lys Ser Asn Arg Leu Val Leu Ala Thr Gly Leu Arg Asn Ser Pro Gln
        35                  40                  45

Arg Glu Arg Arg Arg Lys Lys Arg Gly Leu Phe Gly Ala Ile Ala Gly
    50                  55                  60

Phe Ile Glu Gly Gly Trp Thr Gly Met Val Asp Gly Trp Tyr Gly Tyr
65                  70                  75                  80

His His Gln Asn Glu Gln Gly Ser Gly Tyr Ala Ala Asp Leu Lys Ser
                85                  90                  95

Thr Gln Asn Ala Ile Asp Lys Ile Thr Asn Lys Val Asn Ser Val Ile
            100                 105                 110

Glu Lys Met Asn Thr Gln Phe Thr Ala Val Gly Lys Glu Phe Asn His
        115                 120                 125

Leu Glu Lys Arg Ile Glu Asn Leu Asn Lys Lys Val Asp Asp Gly Phe
    130                 135                 140

Leu Asp Ile Trp Thr Tyr Asn Ala Glu Leu Leu Val Leu Leu Glu Asn
145                 150                 155                 160

Glu Arg Thr Leu Asp Tyr His Asp Ser Asn Val Lys Asn Leu Tyr Glu
                165                 170                 175

Lys Val Arg Asn Gln Leu Lys Asn Asn Ala Lys Glu Ile Gly Asn Gly
            180                 185                 190

Cys Phe Glu Phe Tyr His Lys Cys Asp Asn Thr Cys Met Glu Ser Val
        195                 200                 205

Lys Asn Gly Thr Tyr Asp Tyr Pro Lys Tyr Ser Glu Glu Ala Lys Leu
    210                 215                 220

Asn Arg Glu Glu Ile Asp Gly Val
225                 230

<210> SEQ ID NO 11
<211> LENGTH: 233
```

```
<212> TYPE: PRT
<213> ORGANISM: Influenza A virus

<400> SEQUENCE: 11

Cys Asp Leu Asp Gly Val Lys Pro Leu Ile Leu Arg Asp Cys Ser Val
1               5                   10                  15

Ala Gly Trp Leu Leu Gly Asn Pro Met Cys Asp Glu Phe Ile Asn Val
            20                  25                  30

Pro Glu Trp Ser Tyr Ile Val Glu Lys Ala Asn Pro Ala Asn Asp Leu
        35                  40                  45

Cys Tyr Pro Gly Asn Phe Asn Asp Tyr Glu Glu Leu Lys His Leu Leu
    50                  55                  60

Ser Arg Ile Asn His Phe Glu Lys Ile Gln Ile Ile Pro Lys Ser Ser
65                  70                  75                  80

Trp Ser Asp His Glu Ala Ser Ser Gly Val Ser Ser Ala Cys Pro Tyr
                85                  90                  95

Gln Gly Lys Ser Ser Phe Phe Arg Asn Val Val Trp Leu Ile Lys Lys
            100                 105                 110

Asn Ser Thr Tyr Pro Thr Ile Lys Arg Ser Tyr Asn Asn Thr Asn Gln
        115                 120                 125

Glu Asp Leu Leu Val Leu Trp Gly Ile His His Pro Asn Asp Ala Ala
130                 135                 140

Glu Gln Thr Arg Leu Tyr Gln Asn Pro Thr Thr Tyr Ile Ser Val Gly
145                 150                 155                 160

Thr Ser Thr Leu Asn Gln Arg Leu Val Pro Lys Ile Ala Thr Arg Ser
                165                 170                 175

Lys Val Asn Gly Gln Ser Gly Arg Met Glu Phe Phe Trp Thr Ile Leu
            180                 185                 190

Lys Pro Asn Asp Ala Ile Asn Phe Glu Ser Asn Gly Asn Phe Ile Ala
        195                 200                 205

Pro Glu Tyr Ala Tyr Lys Ile Val Lys Lys Gly Asp Ser Thr Ile Met
    210                 215                 220

Lys Ser Glu Leu Glu Tyr Gly Asn Cys
225                 230

<210> SEQ ID NO 12
<211> LENGTH: 506
<212> TYPE: PRT
<213> ORGANISM: Artificial Sequence
<220> FEATURE:
<223> OTHER INFORMATION: chimeric influenza virus HA polypeptide

<400> SEQUENCE: 12

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
```

```
            100                 105                 110
Lys Ile Gln Ile Ile Pro Lys Ser Ser Trp Ser Asp His Glu Ala Ser
            115                 120                 125

Ser Gly Val Ser Ser Ala Cys Pro Tyr Gln Gly Lys Ser Ser Phe Phe
130             135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
                260                 265                 270

Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
        290                 295                 300

Tyr Val Lys Ser Asn Arg Leu Val Leu Ala Thr Gly Leu Arg Asn Ser
305                 310                 315                 320

Pro Gln Arg Glu Arg Arg Lys Lys Arg Gly Leu Phe Gly Ala Ile
                325                 330                 335

Ala Gly Phe Ile Glu Gly Gly Trp Thr Gly Met Val Asp Gly Trp Tyr
            340                 345                 350

Gly Tyr His His Gln Asn Glu Gln Gly Ser Gly Tyr Ala Ala Asp Leu
            355                 360                 365

Lys Ser Thr Gln Asn Ala Ile Asp Lys Ile Thr Asn Lys Val Asn Ser
    370                 375                 380

Val Ile Glu Lys Met Asn Thr Gln Phe Thr Ala Val Gly Lys Glu Phe
385                 390                 395                 400

Asn His Leu Glu Lys Arg Ile Glu Asn Leu Asn Lys Lys Val Asp Asp
                405                 410                 415

Gly Phe Leu Asp Ile Trp Thr Tyr Asn Ala Glu Leu Leu Val Leu Leu
                420                 425                 430

Glu Asn Glu Arg Thr Leu Asp Tyr His Asp Ser Asn Val Lys Asn Leu
            435                 440                 445

Tyr Glu Lys Val Arg Asn Gln Leu Lys Asn Asn Ala Lys Glu Ile Gly
    450                 455                 460

Asn Gly Cys Phe Glu Phe Tyr His Lys Cys Asp Asn Thr Cys Met Glu
465                 470                 475                 480

Ser Val Lys Asn Gly Thr Tyr Asp Tyr Pro Lys Tyr Ser Glu Glu Ala
                485                 490                 495

Lys Leu Asn Arg Glu Glu Ile Asp Gly Val
            500                 505

<210> SEQ ID NO 13
```

```
<211> LENGTH: 16
<212> TYPE: PRT
<213> ORGANISM: Artificial Sequence
<220> FEATURE:
<223> OTHER INFORMATION: signal peptide

<400> SEQUENCE: 13

Met Glu Lys Ile Val Leu Leu Leu Ala Ile Val Ser Leu Val Lys Ser
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: signal peptide

<400> SEQUENCE: 14

Met Lys Ala Ile Leu Val Val Leu Leu Tyr Thr Phe Ala Thr Ala Asn
1               5                   10                  15

Ala
```

CHIMERIC INFLUENZA VACCINES

CROSS REFERENCE TO RELATED APPLICATIONS

This application claims priority to International Patent Application No. PCT/US21/31406, filed on May 7, 2021, which claims benefit of and priority to U.S. Provisional Application Ser. No. 63/022,328, filed May 8, 2020, all of which are incorporated by reference herein in their entirety for all purposes.

SEQUENCE LISTING

The subject application contains a Sequence Listing which has been filed electronically in ASCII format and is hereby incorporated by reference in its entirety. Said ASCII copy, created on Nov. 7, 2022, is named A1000-00600NP_SeqListing.txt and is 28 kilobytes in size.

FIELD OF THE INVENTION

The present disclosure relates to a chimeric influenza virus hemagglutinin (HA) polypeptide, an immunogenic/vaccine composition containing the same and applications thereof.

BACKGROUND OF THE INVENTION

The traditional method for influenza vaccine production is to culture the virus in specific-pathogen-free (SPF) embryonated hens eggs, and the process often requires more than six months for mass production. However, some vaccine virus strains grow poorly in eggs, and people with allergy to chicken egg could cause safety concerns. New approaches based on cell culturing of viruses have been developed to replace the egg-based method; but the cell-culture method still has a risk of producing potentially hazardous viruses. To overcome these problems, exploration of alternative strategies has demonstrated that recombinant HA-based vaccines can induce neutralizing antibodies against influenza virus infection. However, the antibodies induced by a specific influenza virus subtype usually could not effectively neutralize other influenza subtypes. In addition, the vaccine has to be updated annually because of the constant mutation of the virus.

Therefore, there is still a need to develop a universal vaccine against a wide spectrum of influenza virus strains.

SUMMARY OF THE INVENTION

In one aspect, the present disclosure provides a chimeric influenza virus hemagglutinin (HA) polypeptide, comprising one or more stem domain sequence, each having at least 60% homology with a stem domain consensus sequence of H1 subtype HA (H1 HA) and/or H5 subtype HA (H5 HA), fused with one or more globular head domain sequence, each having at least 60% homology with a globular head domain consensus sequence of H1 subtype HA (H1 HA) or H5 subtype HA (H5 HA).

In some embodiments, the HA is an influenza A HA, an influenza B HA, or an influenza C HA.

In some embodiments, the homology is at least 65%, 70%, 75%, 80%, 85%, 90%, 95%, 96%, 97%, 98%, 99% or 100%.

In some embodiments, the stem domain sequence is an N-terminal stem segment of H1 HA or a C-terminal stem segment of H1 HA; an N-terminal stem segment of H1 HA or a C-terminal stem segment of H1+H5 HA sequences; or an N-terminal stem segment of H5 HA or a C-terminal stem segment of H1+H5 HA sequences.

In some embodiments, the stem domain consensus sequence of H1 HA and/or H5 HA comprises an amino acid sequence of SEQ ID NO: 1, SEQ ID NO: 2, SEQ ID NO: 5, SEQ ID NO: 6, SEQ ID NO: 9, or SEQ ID NO: 10.

In some embodiments, the globular head domain consensus sequence of H1 HA or H5 HA comprises an amino acid sequence of SEQ ID NO: 3, SEQ ID NO: 7, or SEQ ID NO: 11.

In one embodiment, the chimeric influenza virus HA polypeptide comprises an amino acid sequence of SEQ ID NO: 4, SEQ ID NO: 8, or SEQ ID NO: 12.

In some embodiments, one or more glycosites on HA are monoglycosylated. In a further embodiment, the monoglycosylated HA has only N-Acetylglucosamine (GlcNAc) on each glycosite.

In an embodiment, the chimeric influenza virus HA polypeptide is used as an immunogen.

In another aspect, the present disclosure provides an immunogenic composition comprising a chimeric influenza virus HA polypeptide and an adjuvant. In an embodiment, the adjuvant is a glycolipid adjuvant.

In another aspect, the present disclosure provides a recombinant polynucleotide comprising a nucleic acid sequence encoding a polypeptide of the present disclosure and optionally a nucleic acid sequence encoding a signal peptide. In some embodiments, the signal peptide comprises a sequence of SEQ ID NO: 13 or SEQ ID NO: 14.

In another aspect, the present disclosure provides a vector comprising a recombinant polynucleotide of the present disclosure. Also provided is a host cell which comprises a vector of the present disclosure.

In another aspect, the present disclosure provides a method of immunizing a subject against influenza virus comprising administering an effective amount of a chimeric influenza virus hemagglutinin (HA) polypeptide or an immunogenic composition of the present disclosure to the subject.

In another aspect, the present disclosure provides a method of preventing an influenza virus disease in a subject, comprising administering an effective amount of a chimeric influenza virus hemagglutinin (HA) polypeptide or an immunogenic composition of the present disclosure to the subject.

In one embodiment, the methods described herein elicit $CD4^+$ and/or $CD8^+$ T-cell immune responses.

In one embodiment, the methods described herein induce stem-specific antibodies, with higher antibody-dependent cellular cytotoxicity (ADCC), better neutralizing and stronger cross-protection activities against H1, H3, H5 and H7 strains and subtypes.

In one embodiment, the methods described herein enhance the vaccine efficacy with more IFN-γ, TL-4 and CD8+ memory T cells produced.

DETAILED DESCRIPTION OF THE INVENTION

Figure 1:
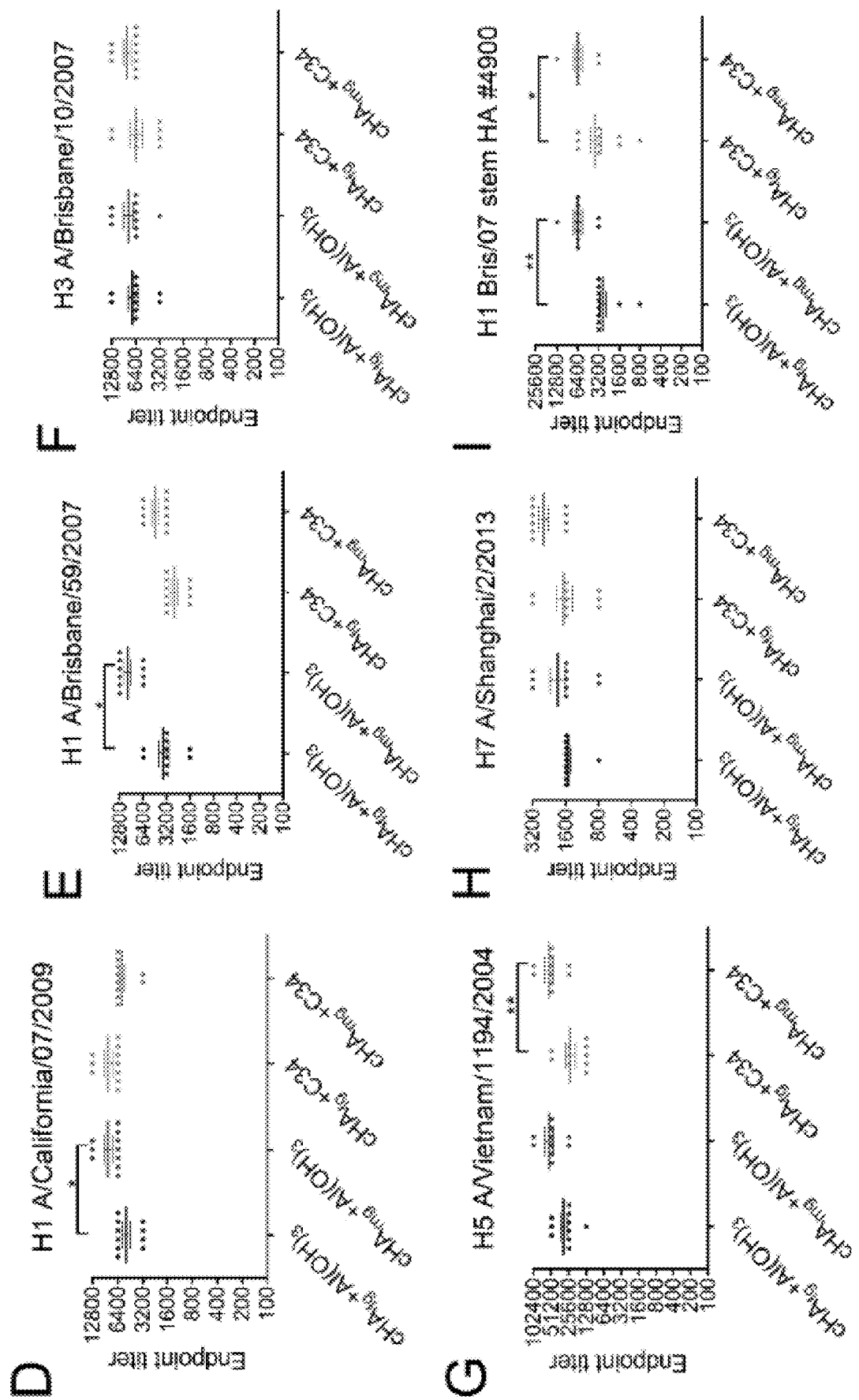
FIGS. 1(A) to (I). The chimeric H5/1 construct with consensus H5 globular head and consensus H1 stem (cHA) and broadly cross-protective, stem-specific antibodies elicited by vaccination with $cHA_{mg}$ immunogens. (A) The constructs of swap H1/5 (H1 globular head and H1+H5 [HA2] stem), swap H5/1 (H5 globular head and H5+H1 [HA2] stem) and chimeric H5/1 (cHA: H5 globular head and H1 stem). (B) Neutralization activity against H1N1 California/07/2009 and H5N1 Vietnam/1194/2004 viruses. (C) The number of granzyme B (GrzB) producing $CD8^+$ T cells in splenocytes stimulated with HA (black bar) or PBS (white bar) control for 2 days in mice vaccinated with PBS (control), HA+Alu, or HA+C34 was evaluated by flow cytometric analysis. (D-I) The antibody titers from the mice vaccinated with $cHA_{fg}$ and $cHA_{mg}$ adjuvanted with $Al(OH)_3$ vs. $cHA_{fg}$ and $cHA_{mg}$ adjuvanted with C34 were measured on day 42 by ELISA with the A/California/07/2009 H1N1 HA protein (D), A/Brisbane/59/2007 H1N1 HA protein (E), A/Brisbane/10/2007 H3N2 HA protein (F), A/Vietnam/1194/2004 H5N1 HA protein (G), A/Shanghai/2/2013 H7N9 HA protein (H) and the A/Brisbane/59/2007 (Bris/07) stem HA (no. 4900) protein (I) as the coating antigen. The endpoint antibody titer was defined as the last dilution of antisera to produce an absorbance 2.5 times higher than the optical absorbance produced by the negative control (pre-immune serum). Data were examined by using Student's t test and two-way ANOVA from Prism; differences were considered statistically significant at *$P<0.05$; **$P<0.01$. Data represent the mean±SEM.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. By Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (TRL Press, 1986); B. Perbal, A Practical Guide To Molecular Cloning (1984); the treatise, Methods in Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods in Cell and Molecular Biology (Mayer and Walker, eds., Academic Press, London, 1987); Antibodies: A Laboratory Manual, by Harlow and Lane s (Cold Spring Harbor Laboratory Press, 1988); and Handbook of Experimental Immunology, Volumes I-IV (D. M. Weir and C. C. Blackwell, eds., 1986).

Definitions

As used in the specification and claims, the singular forms "a", "an" and "the" include plural references unless the context clearly dictates otherwise. For example, the term "a chimeric transmembrane receptor" includes a plurality of chimeric transmembrane receptors.

As used herein, the terms "hemagglutinin" and "HA" refer to any hemagglutinin known to those with skill in the art. In certain embodiments, the hemagglutinin is influenza hemagglutinin, such as an influenza A hemagglutinin, an influenza B hemagglutinin, or an influenza C hemagglutinin. A typical hemagglutinin comprises domains known to those with skill in the art including a signal peptide, a stem domain, a globular head domain, a luminal domain, a transmembrane domain and a cytoplasmic domain.

As used herein, the terms "stem domain polypeptide," "HA stem domain," "influenza virus hemagglutinin stem domain polypeptide" and "HA stalk domain" refer to polypeptide comprising or consisting of one or more polypeptide chains that make up a stem domain of an influenza hemagglutinin. A stem domain polypeptide might be a single polypeptide chain, two polypeptide chains or more polypeptide chains.

As used herein, the terms "influenza virus hemagglutinin head domain polypeptide," "influenza virus hemagglutinin head domain," "HA globular head domain," and "HA head domain" refer to the globular head domain of an influenza hemagglutinin polypeptide.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, glycoproteins, peptides, glycopeptides, glycolipids, polysaccharides, or any combination thereof that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A consensus DNA sequence of avian influenza H5 (pCHA5-II) was used as a vaccine for administration in mice and the result was shown to have a broad protection against various H5 subtypes (Chen, M. W. et al. Broadly neutralizing DNA vaccine with specific mutation alters the antigenicity and sugar-binding activities of influenza hemagglutinin. *Proc. Natl Acad. Sci. USA* 108, 3510-3515 (2011)). The present disclosure reports the design and evaluation of various chimeric vaccines based on the most common avian influenza H5 and human influenza H1 sequences. Of these constructs, the chimeric HA (cHA) vaccine with consensus H5 as globular head and consensus H1 as stem was the best and shown to elicit strong $CD4^+$ and $CD8^+$ T-cell immune responses. Interestingly, the monoglycosylated cHA (cHAmg) vaccine with only GlcNAc on each glycosite induced more stem-specific antibodies, with higher antibody-dependent cellular cytotoxicity (ADCC), better neutralizing and stronger cross-protection activities against H1, H3, H5 and H7 strains and subtypes. Moreover, the cHAmg vaccine combined with a glycolipid adjuvant designed for class switch further enhanced the vaccine efficacy with more IFN-γ, IL-4 and CD8⁺ memory T cells produced.

Chimeric Influenza Virus Hemagglutinin (HA) Polypeptide

The present disclosure provides a chimeric influenza virus hemagglutinin (HA) polypeptide used as immunogen or a vaccine to elicit CD4⁺ and CD8⁺ T-cell immune responses. Accordingly, the chimeric influenza virus HA polypeptide can prevent an influenza virus disease in a subject.

The chimeric influenza virus hemagglutinin (HA) polypeptide of the present disclosure comprises one or more stem domain sequence, each having at least 60% homology with a stem domain consensus sequence of H1 subtype HA (H1 HA) and/or H5 subtype HA (H5 HA) fused with one or more globular head domain sequence, each having at least 60% homology with a globular head consensus sequence of H1 subtype HA (H1 HA) or H5 subtype HA (H5 HA).

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity and identity are quantitative terms that define the degree of sequence match between two compared sequences. In some embodiments, polymeric molecules are considered to be "homologous" to one another if their sequences are at least 60%, 65%, 70%, 75%, 80%, 85%, 90%, 95%, or 99% identical or similar.

In some embodiments the polypeptide according to the present disclosure may comprise one or more sequences having at least 60% homology with a consensus sequence of H1 HA or H5 HA over known human and avian influenza virus strains. In some embodiments, the homology is at least 65%, 70%, 75%, 80%, 85%, 90%, 95%, 96%, 97%, 98%, 99% or 100%. In some embodiments, the stem domain sequence is an N-terminal stem segment of H1 HA or a C-terminal stem segment of H1 HA; an N-terminal stem segment of H1 HA or a C-terminal stem segment of H1+H5 HA sequences; or an N-terminal stem segment of H5 HA or a C-terminal stem segment of H1+H5 HA sequences.

In some embodiments, the stem domain consensus sequence of H1 HA and/or H5 HA comprises an amino acid sequence of SEQ ID NO: 1, SEQ ID NO: 2, SEQ ID NO: 5, SEQ ID NO: 6, SEQ ID NO: 9, or SEQ ID NO: 10.

```
(H1 STEM)
                                        SEQ ID NO: 1
    DTLCIGYHANNSTDTVDTVLEKNVTVTHSVNLLEDKHNGKL (H1 STEM)
                                        SEQ ID NO: 2
NTTCQTPKGAINTSLPFQNIHPITIGKCPKYVKSTKLRLATGLRNVPSI

QSRGLFGAIAGFIEGGWTGMVDGWYGYHHQNEQGSGYAADLKSTQNAID
```

```
KITNKVNSVIEKMNTQFTAVGKEFNHLEKRIENLNKKVDDGFLDIWTYN

AELLVLLENERTLDYHDSNVKNLYEKVRNQLKNNAKEIGNGCFEFYHKC

DNTCMESVKNGTYDYPKYSEEAKLNREEIDGVKLESTRIYQ (H1 STEM)
                                        SEQ ID NO: 5
    DTLCIGYHANNSTDTVDTVLEKNVTVTHSVNLLEDKHNGKL (H1+H5 STEM)
                                        SEQ ID NO: 6
NTTCQTPKGAINTSLPFQNIHPITIGKCPKYVKSTKLRLATGLRNVPSI

QSRGLFGAIAGFIEGGWQGMVDGWYGYHHSNEQGSGYAADKESTQKAID

GVTNKVNSIIDKMNTQFEAVGREFNNLERRIENLNKKMEDGFLDVWTYN

AELLVLMENERTLDFHDSNVKNLYDKVRLQLRDNAKELGNGCFEFYHKC

DNECMESVRNGTYDYPQYSEEARLKREEISGV (H5 STEM)
                                        SEQ ID NO: 9
    DQICIGYHANNSTEQVDTIMEKNVTVTHAQDILEKTHNGKL (H5+H1 STEM)
                                        SEQ ID NO: 10
NTKCQTPMGAINSSMPFHNIHPLTIGECPKYVKSNRLVLATGLRNSPQR

ERRRKKRGLFGAIAGFIEGGWTGMVDGWYGYHHQNEQGSGYAADLKSTQ

NAIDKITNKVNSVIEKMNTQFTAVGKEFNHLEKRIENLNKKVDDGFLDI

WTYNAELLVLLENERTLDYHDSNVKNLYEKVRNQLKNNAKEIGNGCFEF

YHKCDNTCMESVKNGTYDYPKYSEEAKLNREEIDGV
```

In one embodiment, the globular head domain consensus sequence of H1 HA or H5 HA comprises an amino acid sequence of SEQ ID NO:3, SEQ ID NO:7 or SEQ ID NO:11.

```
(H5 GLOBULAR HEAD)
                                        SEQ ID NO: 3
CDLDGVKPLILRDCSVAGWLLGNPMCDEFINVPEWSYIVEKANPANDLC

YPGNFNDYEELKHLLSRINHFEKIQIIPKSSWSDHEASSGVSSACPYQG

KSSFFRNVVWLIKKNSTYPTIKRSYNNTNQEDLLVLWGIHHPNDAAEQT

RLYQNPTTYISVGTSTLNQRLVPKIATRSKVNGQSGRMEFFWTILKPND

AINFESNGNFIAPEYAYKIVKKGDSTIMKSELEYGNC (H1 GLOBULAR HEAD)
                                        SEQ ID NO: 7
CKLRGVAPLHLGKCNIAGWILGNPECESLSTASSWSYIVETSSSDNGTC

YPGDFIDYEELREQLSSVSSFERFEIFPKTSSWPNHDSNKGVTAACPHA

GAKSFYKNLIWLVKKGNSYPKLSKSYINDKGKEVLVLWGIHHPSTTADQ

QSLYQNADAYVFVGTSRYSKKFKPEIAIRPKVRDQEGRMNYYWTLVEPG

DKITFEATGNLVVPRYAFAMERNAGSGIIISDTPVHDC
```

(H5 GLOBULAR HEAD)
SEQ ID NO: 11
CDLDGVKPLILRDCSVAGWLLGNPMCDEFINVPEWSYIVEKANPANDLC

YPGNFNDYEELKHLLSRINHFEKIQIIPKSSWSDHEASSGVSSACPYQG

KSSFFRNVVWLIKKNSTYPTIKRSYNNTNQEDLLVLWGIHHPNDAAEQT

RLYQNPTTYISVGTSTLNQRLVPKIATRSKVNGQSGRMEFFWTILKPND

AINFESNGNFIAPEYAYKIVKKGDSTIMKSELEYGNC

In one embodiment, the chimeric influenza virus HA polypeptide comprises an amino acid sequence of SEQ ID NO: 4, SEQ ID NO: 8, or SEQ ID NO: 12.

(Chimeric H5/1)
SEQ ID NO: 4
DTLCIGYHANNSTDTVDTVLEKNVTVTHSVNLLEDKHNGKLCDLDGVKP

LILRDCSVAGWLLGNPMCDEFINVPEWSYIVEKANPANDLCYPGNFNDY

EELKHLLSRINHFEKIQIIPKSSWSDHEASSGVSSACPYQGKSSFFRNV

VWLIKKNSTYPTIKRSYNNTNQEDLLVLWGIHHPNDAAEQTRLYQNPTT

YISVGTSTLNQRLVPKIATRSKVNGQSGRMEFFWTILKPNDAINFESNG

NFIAPEYAYKIVKKGDSTIMKSELEYGNCNTTCQTPKGAINTSLPFQNI

HPITIGKCPKYVKSTKLRLATGLRNVPSIQSRGLFGAIAGFIEGGWTGM

VDGWYGYHHQNEQGSGYAADLKSTQNAIDKITNKVNSVIEKMNTQFTAV

GKEFNHLEKRIENLNKKVDDGFLDIWTYNAELLVLLENERTLDYHDSNV

KNLYEKVRNQLKNNAKEIGNGCFEFYHKCDNTCMESVKNGTYDYPKYSE

EAKLNREEIDGVKLESTRIYQ (Swap H1/5)
SEQ ID NO: 8
DTLCIGYHANNSTDTVDTVLEKNVTVTHSVNLLEDKHNGKLCKLRGVAP

LHLGKCNIAGWILGNPECESLSTASSWSYIVETSSSDNGTCYPGDFIDY

EELREQLSSVSSFERFEIFPKTSSWPNHDSNKGVTAACPHAGAKSFYKN

LIWLVKKGNSYPKLSKSYINDKGKEVLVLWGIHHPSTTADQQSLYQNAD

AYVFVGTSRYSKKFKPEIAIRPKVRDQEGRMNYYWTLVEPGDKITFEAT

GNLVVPRYAFAMERNAGSGIIISDTPVHDCNTTCQTPKGAINTSLPFQN

IHPITIGKCPKYVKSTKLRLATGLRNVPSIQSRGLFGAIAGFIEGGWQG

MVDGWYGYHHSNEQGSGYAADKESTQKAIDGVTNKVNSIIDKMNTQFEA

VGREFNNLERRIENLNKKMEDGFLDVWTYNAELLVLMENERTLDFHDSN

VKNLYDKVRLQLRDNAKELGNGCFEFYHKCDNECMESVRNGTYDPQYS

EEARLKREEISGV (Swap H5/1)
SEQ ID NO: 12
DQICIGYHANNSTEQVDTIMEKNVTVTHAQDILEKTHNGKLCDLDGVKP

LILRDCSVAGWLLGNPMCDEFINVPEWSYIVEKANPANDLCYPGNFNDY

EELKHLLSRINHFEKIQIIPKSSWSDHEASSGVSSACPYQGKSSFFRNV

VWLIKKNSTYPTIKRSYNNTNQEDLLVLWGIHHPNDAAEQTRLYQNPTT

-continued
YISVGTSTLNQRLVPKIATRSKVNGQSGRMEFFWTILKPNDAINFESNG

NFIAPEYAYKIVKKGDSTIMKSELEYGNCNTKCQTPMGAINSSMPFHNI

HPLTIGECPKYVKSNRLVLATGLRNSPQRERRRKKRGLFGAIAGFIEGG

WTGMVDGWYGYHHQNEQGSGYAADLKSTQNAIDKITNKVNSVIEKMNTQ

FTAVGKEFNHLEKRIENLNKKVDDGFLDIWTYNAELLVLLENERTLDYH

DSNVKNLYEKVRNQLKNNAKEIGNGCFEFYHKCDNTCMESVKNGTYDYP

KYSEEAKLNREEIDGV

In some embodiments, to enhance the immunogenicity, one or more glycosites on HA are monoglycosylated. Preferably, the monoglycosylated HA has only N-Acetylglucosamine (GlcNAc) on each glycosite.

The chimeric influenza virus HA polypeptide may be produced by any suitable method, many of which are known to those skilled in the art. For example, the proteins may be chemically synthesized, or produced using recombinant DNA technology (e.g. in bacterial cells, in cell culture (mammalian, yeast or insect cells), in plants or plant cells, or by cell-free prokaryotic or eukaryotic-based expression systems, by other in vitro systems, etc.) Accordingly, the present disclosure provides a recombinant polynucleotide comprising a nucleic acid sequence encoding a polypeptide of the present disclosure and optionally a nucleic acid sequence encoding a signal peptide. The present disclosure provides a vector comprising a recombinant polynucleotide of the present disclosure. The embodiments of the polypeptide of the present disclosure are described herein. In one embodiment, the signal peptide comprises a sequence of SEQ ID NO: 13 (MEKIVLLLAIVSLVKS) or SEQ ID NO: 14 (MKATLVVLLYTFATANA). A host cell comprising a vector of the present disclosure is also provided.

Immunogenic Compositions

The immunogenic composition preferably comprises at least one pharmaceutically acceptable carrier and/or adjuvant. In one embodiment, the adjuvant is a glycolipid adjuvant. Examples of the adjuvant include, but are not limited to, Al(OH)$_3$, AlPO$_4$, C34, squalene and QS21.

A chimeric influenza virus HA polypeptide of the present disclosure may be formulated or administered in combination with one or more pharmaceutically-acceptable excipients. Immunogenic/vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

The immunogenic composition is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable but may include an initial administration followed by subsequent administrations. The dosage of the vaccine may also depend on the route of administration and varies according to the size of the host.

Formulations of the vaccine compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Applications

It has been known for some time that cytotoxic T lymphocytes (CTL) may provide an immune response against influenza virus strains. Recent studies have shown that a CTL response in humans may be directed towards multiple epitopes.

Provided herein are methods for prevention of an influenza virus disease in humans and other mammals. Also provided is a method of eliciting an immune response in a subject against influenza virus. The method involves administering an effective amount of a chimeric influenza virus HA polypeptide or an immunogenic composition/vaccine of the present disclosure to the subject, thereby inducing in the subject an immune response specific to influenza virus strains (such as H1, H3, H5 and H7 strains and subtypes). Preferably, the methods elicit $CD4^+$ and $CD8^+$ T-cell immune responses. More preferably, the methods induce stem-specific antibodies, with higher antibody-dependent cellular cytotoxicity (ADCC), better neutralizing and stronger cross-protection activities against H1, H3, H5 and H7 strains and subtypes. The methods also enhance the vaccine efficacy with more IFN-γ, IL-4 and CD8+ memory T cells produced.

The antibody titer in the subject is increased following vaccination. In exemplary aspects, the immune compositions or vaccines of the present disclosure are used to provide prophylactic protection from influenza. Prophylactic protection from influenza can be achieved following administration of a vaccine or combination vaccine, of the present disclosure. Vaccines (including combination vaccines) can be administered once, twice, three times, four times or more but it is likely sufficient to administer the vaccine once (optionally followed by a single booster). Dosing may need to be adjusted accordingly.

A prophylactically effective dose is a therapeutically effective dose that protects against the influenza virus at a clinically acceptable level. In some embodiments the therapeutically effective dose is a dose listed in a package insert for the vaccine.

The chimeric influenza virus HA polypeptide or an immunogenic composition/vaccine of the present disclosure may be administered by any route which results in a therapeutically effective outcome. These include, but are not limited to, intradermal, intramuscular, and/or subcutaneous administration. In some embodiments, a chimeric influenza virus HA polypeptide or an immunogenic composition/vaccine of the present disclosure may be administered intramuscularly or intradermally, similarly to the administration of inactivated vaccines known in the art.

This invention is not limited in its application to the details of construction and the arrangement of components set forth in the following description or illustrated in the drawings. The invention is capable of other embodiments and of being practiced or of being carried out in various ways.

EXAMPLES

Methods

Vaccine and plasmid construction. All 102 full-length HA sequences from H1N1 viruses available in early 2009-2013 were downloaded from the NCBI database and aligned by the ClustalW algorithm from the BioEdit program. The most conserved amino acid at each position was chosen to create a consensus H1 sequence. The consensus hemagglutinin H5 (pCHA5-II) sequence was generated as described previously. The nucleotide sequences of consensus hemagglutinin H5 (pCHA5-II) and consensus H1 were cloned into the pcDNA expression vector, and the resulting plasmids were used as the templates for swap and chimeric HA construction. Swap H1/5 is composed of H1 as HA1 (amino acid 1~327 of SEQ ID NO: 8) and H5 as HA2 (amino acid 328~503 of SEQ ID NO: 8), giving H1 as globular head and H1+H5 (HA2) stem. Swap H5/1 is composed of H5 as HA1 (amino acid 1~330 of SEQ ID NO: 12) and H1 as HA2 (amino acid 331~506 of SEQ ID NO: 12), giving H5 as globular head and H5+H1 (HA2) stem. For chimeric H5/1 construct, the globular head domain is composed of the amino acid sequence between residues C42 and C274 of SEQ ID NO: 4 (H3 numbering) and the stem region is comprised of portions of HA1 and HA2 subunits (amino acids 1~41 of SEQ ID NO: 4 and 275~511 of SEQ ID NO: 4). The transmembrane domain was replaced with the additional residues from the bacteriophage T4 fibritin foldon trimerization sequence, thrombin cleavage site and $(His)_6$-tag at the C-terminus of the HA. Both DNA sequences of consensus HA were optimized for expression by using human-preferred codons and various regions were amplified by PCR and subsequently cloned into the pcDNA vector for expression. Furthermore, the HA gene from influenza virus seasonal H1N1 Brisbane/59/2007, pandemic H1N1 California/07/2009, H3N2 Brisbane/10/2007, H7N9 A/Shanghai/2/2013 and avian flu H5N1 Vietnam/1194/2004 were also optimized, synthesized, and cloned into the pcDNA expression vector. The sequences were confirmed by DNA sequencing and prepared in high quality for protein expression and purification.

Expression of recombinant secreted HA from expressed cells. Human epithelial kidney (HEK) 293T and HEK293S cells were routinely maintained in DMEM (Gibco) supplemented with 10% fetal bovine serum (Gibco). For transient transfection, 293T or 293S cells were seeded in a 10 cm dish (Nunc, Roskilde, Denmark) and all the procedures were performed according to the manufacture's protocol. Briefly, 293T or 293S cells at 80% confluency were transfected with Mirus TransIT©-LT1 (Mirus Bio) transfection reagent using a 3:1 ratio of reagent to plasmid DNA. TransIT©-LT1 reagents were diluted with Opti-MEM (Gibco) and the mixture was incubated for 5-20 minutes at room temperature. The solution was added with plasmid DNA and mixed completely followed by incubation for 15-30 minutes. Prior to transfection, cells were replaced with fresh DMEM (Gibco) medium supplemented with 10% fetal bovine serum. The TransIT©-LT1 reagent/DNA complex was added to the cells and incubated for 48 h at 37° C. The expression of hemagglutinin was confirmed with immunoblots using anti-$(his)_6$ antibodies (Qiagen) or specific anti-hemagglutinin antibodies and the horseradish peroxidase (HRP)-conjugated secondary antibodies (PerkinElmer).

Purification of recombinant secreted hemagglutinins. For expression in human 293T cells, pcDNA carrying the gene of interest was prepared in high quality and transfected to the cells with Mirus TransIT©-LT1 (Mirus Bio). After 48 h of transfection, the medium was collected and the cells were clarified by centrifugation at 1,000×g for 10 mins. The supernatant was purified by Ni-NTA (nickel-nitrilotriacetic acid) affinity column (GE Healthcare). The supernatants were loaded onto Ni-NTA affinity column pre-equilibrated in 20 mM Tris-HCl pH 8.0 and 300 mM NaCl. The unbound proteins were washed out with imidazole gradient from 25 to 50 mM in 20 mM Tris-HCl pH 8.0 and 300 mM NaCl (Buffer A). Then, the HA protein was eluted with 100 to 300 mM imidazole gradient in Buffer A. The purified HA proteins were concentrated by Amicon Ultrafiltration Unit (MW30K cutoff) (Millipore) in PBS, pH 7.4. The purity was monitored by using SDS-PAGE and the proteins were confirmed using Western blot with anti-(his)$_6$ antibodies (Qiagen) or specific anti-hemagglutinin antibodies and the horseradish peroxidase-conjugated secondary antibodies (PerkinElmer). Finally, the trimer form of HA proteins was obtained by using size-exclusion column, Superdex 200 Increase 10/300 GL gel filtration column (GE Healthcare).

Preparation of mono-glycosylated HA proteins. HEK293S cells, which are deficient in N-acetylglucosaminyltransferase I, were used to produce HA with high-mannose glycans[31]. The purified HA protein from HEK293S cells was treated with Endo H (NEB) at 20° C. for overnight to produce the monoglycosylated $HA_{mg}$. The ratio of proteins to Endo H was 3 to 1 (w/v) for HA. Endo H and mono-glycosylated HA protein were then separated by Superdex 200 Increase 10/300 GL gel filtration column (GE Healthcare). The $HA_{mg}$ proteins were concentrated by Amicon Ultrafiltration Unit (MW30K cutoff) (Millipore) in PBS, pH 7.4 and confirmed by SDS-PAGE and LC-MS/MS analysis.

Identification of N-linked glycosylation on HA proteins. Ten micrograms of protein were run on SDS-PAGE and were prepared for in-gel digestion. The desired proteins bands were excised with a sharp scalpel, diced into 1 mm pieces and placed into 1.3 ml eppendorf tubes. After washing twice with 500 µl of 25 mM ammonium bicarbonate in 50% ACN (acetonitrile) for 3 min, the gel pieces were dried using a SpeedVac evaporator (Thermo). The dried samples were reduced by the addition of 100 µl of 50 mM dithiothreitol (DTT) in 25 mM ammonium bicarbonate (pH 8.5) at 37° C. for 1 h followed by centrifuge at 10,000 g for 1 min. The solution was removed and the gel samples were proceeded to an alkylation step by the addition of 100 µl of 100 mM iodoacetamide (IAA) in 25 mM ammonium bicarbonate (pH 8.5) and incubated in the dark at room temperature for 1 h. After washing with 500 µl of 50% acetonitrile in 25 mM ammonium bicarbonate (pH 8.5) and 500 µl of 100% acetonitrile, the samples were centrifuged at 10,000 g for 1 min and the supernatant was removed completely. The gel samples were dried at a SpeedVac evaporator and redissolved with 200 µl of 25 mM ammonium bicarbonate (pH 8.5). Gel samples were then treated with 0.5 µg trypsin (Promega, Madison, WI, USA) and 1 µg chymotrypsin (Promega, Madison, WI, USA) for overnight. After an overnight digestion, the samples were added with 100 µl of 50% acetonitrile in 5% TFA. The samples were sonicated for 10 sec, and then stopped for 10 sec. The processes were repeated 10 times. The supernatant containing peptide mixtures was removed from the sample tubes and transferred to new tubes. The procedure was repeated twice. The combined supernatants were dried in SpeedVac concentrator and processed for LC-MS/MS analysis.

Endotoxin measurement. Endotoxin levels were determined using the Pierce® LAL Chromogenic Endotoxin Quantitation Kit (Thermo Scientific). Protein samples were diluted in 10, 20, 100, and 1000-fold, while endotoxin standards were prepared as 10, 5, 2.5, 1.25, 0.63, 0.31, 0.15, and 0 ng/ml. After the microplate was equilibrated in a heating block for 10 mins at 37° C., protein samples or standards were mixed with Limulus Amebocye Lasate (LAL) Pyrochrome reagent (final volume 100 µl) (1:1) in endotoxin-free wells at 37° C. for 10 minutes. One hundred µls of substrate solution were added to each well and the plates were incubated at 37° C. for 6 mins. The reaction was stopped with the addition of 50 µl stop reagent (25% acetic acid). The absorbance of wells was measured at 405 nm using a SpectraMax M5 (Molecular Devices, Sunnyvale, CA, USA). A standard curve was obtained by plotting the absorbance versus the corresponding concentrations of the standards. The standard curve was used to determine the endotoxin concentration of the samples. Endotoxin values of all purified proteins were <0.5 ng/ml.

Mice vaccination. Adjuvant C34 was chemically synthesized as described and dissolved in DMSO. Female 6- to 8-week-old BALB/c mice (n=10 per group) were immunized intramuscularly with 20 µg of purified chimeric $HA_{fg}$ or $HA_{mg}$ proteins in PBS, pH 7.4, and mixed with 50 µg of aluminum hydroxide (Alum; Sigma) or 2 µg of C34. Control mice were injected with phosphate buffer saline (PBS). Three vaccinations were given at two-week intervals. Blood was collected 14 days after the second or third immunization. The blood was incubated at 37° C. for 30 minutes, and centrifuged at 1,2000 rpm for 10 mins to collect serum. The HA-specific antibodies in serum collected from vaccinated mice were assessed by enzyme-linked immunosorbent assay (ELISA) and neutralization assay.

Determination of HA-specific antibodies by ELISA. HA-specific antibody titers were detected by ELISA using H1N1 A/Brisbane/59/2007, H1N1 A/California/07/2009, H3N2 Brisbane/10/2007, H7N9 A/Shanghai/2/2013 and H5N1 Vietnam/1194/2004 HA proteins as the substrates. Ninety-six-well ELISA plate (Greiner bio-one, Frickenhausen, Germany) was coated with 100 µl of protein diluted in ELISA coating buffer, 100 mM sodium bicarbonate (pH 8.8), at a concentration of 5 µg/ml per well, and covered with a plastic sealer at 4° C. for overnight. After the plates were blocked with 1% BSA in TBST (137 mM NaCl, 20 mM Tris-base, 0.05% Tween 20, pH 7.4) at 37° C. for 1 h and washed 3 times with TBST, the plates were incubated with 200 µl of mouse serum in 2-fold serial dilutions at 37° C. for 2 h. After serum was moved and the plate was washed 6 times, HA-specific IgG was monitored by using 200 µl of secondary HRP-labeled anti-mouse antibody (1:8000) (PerkinElmer, Waltham, MA, USA). After 1 h of incubation at 37° C., the plates were washed 6 times with TBST and developed with 100 µl of the Super Aquablue ELISA substrate (eBioscience, San Diego, CA, USA) for 1 min. The reaction was stopped with the addition of 100 µl of 0.625 M oxalic acid. The absorbance of wells was measured at 405 nm using a SpectraMax M5 (Molecular Devices, Sunnyvale, CA, USA). The endpoint antibody titer was defined as the highest dilution of serum to produce an absorbance 2.5 times higher than the optical absorbance (OD) produced by the negative control (pre-immune serum). The background endpoint antibody titer was assigned as less than 1:50.

Harvest of bone marrow-derived dendritic cells. The GM-CSF-cultured bone marrow-derived dendritic cells (BMDCs) were prepared as described previously. Briefly, bone marrow single cell suspensions were subjected to RBC lysis to remove the red blood cells (RBCs). The remaining cells were cultured in 10 ml of RPMI 1640 supplemented with 20 ng/mL murine GM-CSF (eBioscience), 10% FBS (BenchMark), 50 µM 2-ME, 100 units/mL penicillin, and 100 µg/mL streptomycin. Cells were plated into each petri dish to achieve the final cell density of $2 \times 10^6$ cells/petridish.

The culture was replenished by adding 10 ml of fresh culture medium containing 20 ng/mL murine GM-CSF at day 3 and refreshed with one-half the volume of complete culture medium as described above at day 6. At day 8, immature BMDCs were harvested by collecting nonadherent cells by gently pipetting and re-plated the cells at a density of $10^6$/ml. For CD8+ T cell assay, immature BMDCs were co-cultured with CD8+ T cell and chimeric HA proteins (0.1 mg/well in 100 µL) for 48 h. The number of granzyme B producing CD8+ T cells was determined by flow cytometric analysis after washing.

Enzyme-linked immunospot (ELISpot) assay. ELISPOT plates were coated with anti-mouse IFN-γ, IL-4 (Mabtech AB, Stockholm, Sweden) or granzyme B (R&D Systems) according to the manufacturer's instructions. The plates were washed four times and incubated for 30 min with RPMI-1640 supplemented with 10% Fetal bovine serum (Gibco). For the detection of IFN-γ, IL-4 and granzyme B-secreting cells from chimera-immunized mice, splenocytes were collected and cultured at $5\times10^5$ per well at 37° C. in 5% $CO_2$ for 24 h with specific peptides from HA for restimulation. The cells were removed and incubated with biotinylated anti-mouse IFN-γ, IL-4 (Mabtech AB) or granzyme B (R&D Systems) specific antibody. The plates were washed five times before the addition of streptavidin-ALP conjugate and developed with ready-to-use BCIP/NPT substrate. Following drying, the number of resulting spots was analyzed with an Immune Spot Reader (Cellular Technology Ltd.). Data were obtained from triplicate wells.

Neutralization assay. The culture supernatant containing 100 $TCID_{50}$ of virus was mixed with equal volume of two-fold serially diluted serum and incubated at 37° C. for 1 h. The mixtures were then added to MDCK cells in each well of a 96-well plate and incubated at 37° C. for 3 days. The cells were added 30 µl of CellTiter-Glo (Promega) to determine the number of viable cells based on quantitation of the ATP present. The neutralizing activity of serum was determined as the maximal dilution fold that significantly protected cells from virus-induced death.

Microneutralization assay. An infection medium (DMEM supplemented with 0.3% BSA, 2 µg/ml TPCK-Trypsin) containing virus at 100 $TCID_{50}$ was mixed in equal volume with two-fold serial dilutions of serum and incubated at 37° C. for 1 h. The mixture was then added to MDCK cells ($1.5\times10^4$ cells per well) in each well of a 96-well plate and incubate at 37° C. for 16-20 h. The cells were washed with PBS, fixed in acetone/methanol solution (vol/vol 1:1), and blocked with 5% skim milk. After 1 h of incubation at 37° C., the wells were washed 6 times with PBST, and the virus titer was monitored by using 100 µl of mAb against influenza A NP (1:2500). After 1 h of incubation at 37° C., the wells were washed 6 times with PBST and added 100 µl of secondary HRP-labeled anti-rabbit antibody (1:5000) (PerkinElmer, Waltham, MA, USA). After 1 h of incubation at 37° C., the wells were washed 6 times with PBST again and developed with 50 µl of the 1-Step Ultra TMB substrate (Thermo) for 1 min. The reaction was stopped with the addition of 50 µl of 1 M $H_2SO_4$. The absorbance of wells was measured at 450 nm using a SpectraMax M5 (Molecular Devices, Sunnyvale, CA, USA).

Antibody dependent cell mediated cytotoxicity reporter assay. MDCK cells ($1\times10^4$ cells per well) in each well of a 96-well flat-bottom plate were incubated at 37° C. for 24 h. The next day, $1\times10^4$ MDCK cells were infected with influenza viruses at multiplicity of infection (MOI) of 1 for 24 h. The medium was then replaced with Roswell Park Memorial Institute (RPMI) medium 1640 supplemented with 4% Low IgG Serum followed by addition of serial dilutions of antisera from chimeric HA protein-vaccinated mice and incubated at 37° C. for 30 min. Jurkat effector cells expressing mouse FcγRIII (Promega) were suspended in RPMI 1640 medium containing 4% low IgG FBS and the target cells: effector cells ratio of 1:5 were added to the infected MDCK cells. After incubation at 37° C. for 6 h, assay plates were removed from the 37° C. incubator and equilibrated for 15 min at ambient temperature before Bio-Glo™ Luciferase Assay Buffer (Promega) was added in a 1:1 ratio. Luminescence was measured on a CLARIOstar plate-reader.

Virus challenge experiments. Two weeks after three vaccinations at two week intervals, the immunized mice were challenged intranasally with 10 $LD_{50}$ (the virus doses leading to 50% of the death of mice) of H1N1 California/07/2009, H1N1 A/New Caledonia/1999, H1N1 A/WSN/1933, H1N1 A/Solomon Islands/03/2006 and a reassortant H5N1 virus A/Vietnam/1194/2004/NIBRG14 and H5N1 A/Turkey/1/2005/NIBRG23. After infection, the mice were observed daily for 14 days, and survival and body weight were recorded. The percentage of body weight was calculated for each individual animal per group by comparing the daily weight to the pre-challenge weight, and mice losing more than 25% of their initial weight were sacrificed and scored as dead. Mouse studies were approved by the Institutional Animal Care and Use Committee of Academia Sinica. All animal experiments were performed under biosafety level-3 enhancement conditions.

Expression and purification of recombinant F10 antibodies. The plasmid that encodes the F10 antibody was transfected into serum-free adapted FreeStyle™ 293F cells by using polyethyleneimine and was cultured in FreeStyle™ 293 Expression Medium (Gibco) in 125 ml sterile Erlenmeyer flasks, rotating at 135 rpm on an orbital shaker platform. The supernatant was collected 72 h after transfection and the cells were clarified by centrifugation at 1,000×g for 10 mins. The supernatants were loaded onto Protein-A column (GE Healthcare) that was pre-equilibrated in 5 Column Volumes (CV) of phosphate buffered saline (PBS) washing buffer (pH 7.0), followed by 5 CV of washing buffer. The F10 antibody was eluted with 0.2 M glycine buffer (pH 2.5) and the fractions were collected into tubes containing 0.5 mL 1 M Tris-HCl pH 9.0 for neutralization. The purity was monitored by using SDS-PAGE.

Statistical analysis. The animal experiments used for evaluation of immune responses were repeated at least three times (n=5 per group), and the virus challenge studies were done at least twice (n=10 per group). The response of each mouse was counted as an individual data point for statistical analysis. Data obtained from animal studies were examined by using two-way ANOVA from Prism; data were presented as mean±SEM and differences were considered significant at *P<0.05; P<0.01; *P<0.001.

Example 1 Preparation and Characterization of Monoglycosylated Chimeric HA

To design a universal vaccine, we first aimed to have a vaccine with broad protection against influenza A virus group 1 (H1 and H5 are the major subtypes while H2, H6, and H9 are minor). Therefore, the HA sequences from H1N1 viruses available from early 2009 to 2013 were used to create a consensus H1 sequence. The consensus H5 and consensus H1 were then used as the templates for vaccine design. In influenza virus replication, the HA precursor (HA0) is proteolytically cleaved into two subunits, HA1 and HA2; the HA1 subunit carries the 5-N-acetylneuraminic acid (sialic acid) binding site, and the HA2 subunit is responsible for virus fusion with the host cellular membrane (FIG. 5A). On the other hand, HA can be divided into two structural domains, globular head and stem, based on the three-dimensional (3D) structure. The stem region contains the HA2 domain, the N-terminal 36~50 residues and a short stretch of the C terminus of the HA1 domain. We thus designed the vaccines based on various combinations of domains from H1 and H5. We first generated the swap H1/5 (H1 globular head and [H1+H5(HA2) stem], swap H5/1 (H5 globular head and [H5+H1(HA2) stem], and chimeric H5/1 (H5 globular head and H1 stem) for comparison (FIG. 1A and FIG. 5A). The result indicated that immunization with consensus H1N1 and swap H1/5 did not induce cross-protective activities, but the swap H5/1 and chimeric H5/1 did elicit cross-neutralization activity against H1N1 and H5N1 viruses (FIG. 1B). We next investigated whether this cross-protection was contributed from the $CD8^+$ T cell response, and found that granzyme B was more secreted in chimeric H5/1-immunized mice, suggesting that the chimeric H5/1 vaccine induced stronger $CD8^+$ T cell response compared to the swap H5/1 vaccine (FIG. 1C).

Example 2 Effect of Glycosylation on the Immune Response of Chimeric H5/1 (cHA)

Figure 5:
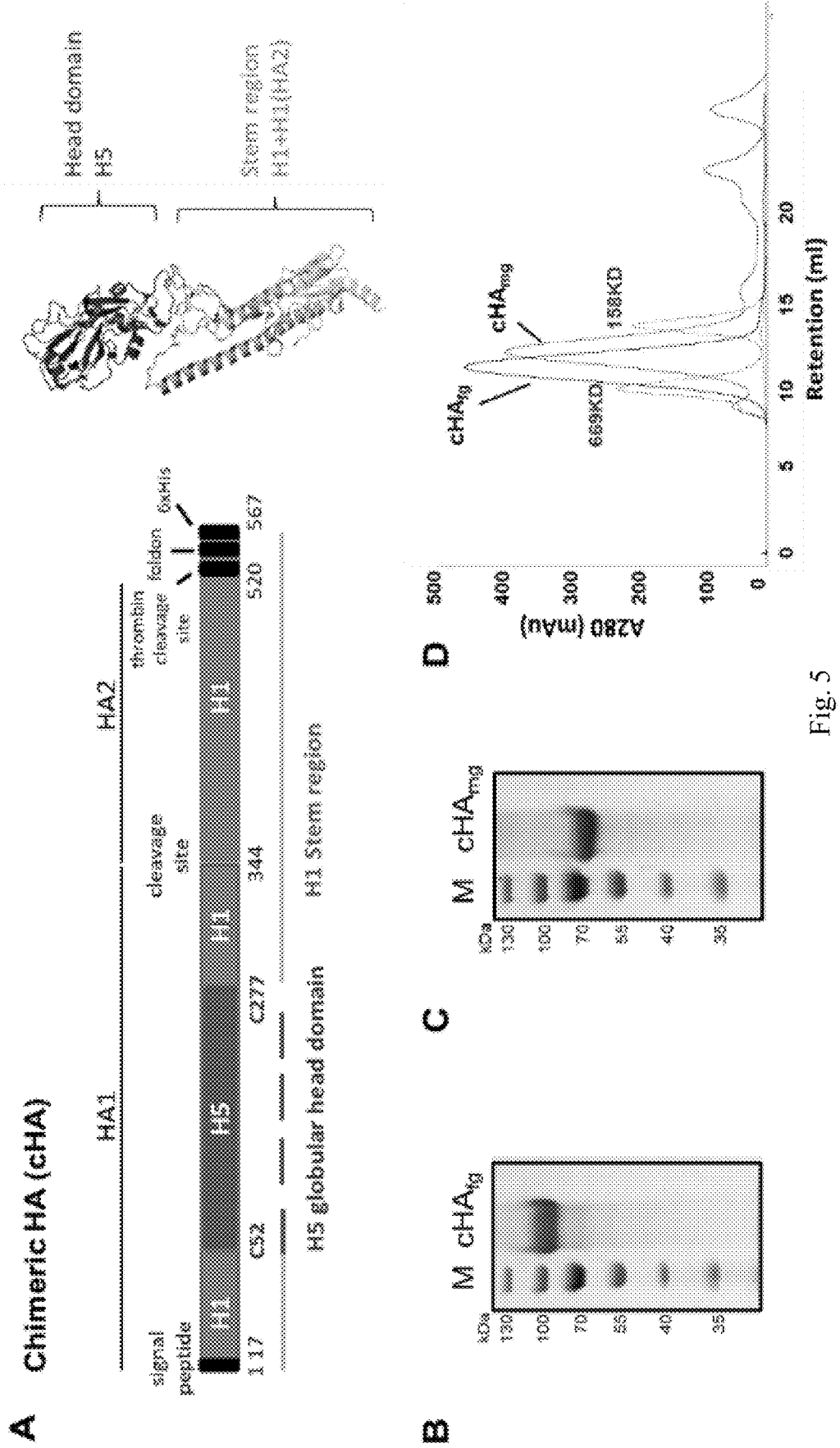
FIGS. 5(A) to (E). Design and preparation of chimeric HA proteins. (A) The designed influenza HA sequences were constructed using the consensus H1N1 sequence and the consensus H5N1 sequence pCHA5-II to generate the chimeric HA. The globular head domain is composed of the amino acid sequence between residues C52 and C277 (H3 numbering). The stem region is composed of portions of HA1 and HA2 subunits. The protein structures were downloaded from the Protein Data Bank ID code 2IBX (VN1194 H5 HA) and 3LZG (A/California/04/2009). Final images were generated with PyMol. Because no structure of a consensus HA has been published, the image of the head domain of the avian flu H5 (Vietnam/1194/2004) and the stem region of the pandemic H1N1 (California/07/2009) are used for the chimeric HA construct. (B-D) Purification of chimeric HA protein and gel-1 filtration chromatography analysis. (B) The purified HA proteins were analyzed by SDS/PAGE. M: molecular weight marker. left: $cHA_{fg}$, the fully glycosylated cHA directly purified from HEK293T cells; (C) $cHA_{mg}$, the monoglycosylated cHA purified from HEK293S cells and digested with endoglycosidase H. (D) Gel filtration analysis of purified secreted HA proteins. The fully glycosylated cHA from HEK293T cells and the monoglycosyalted cHA existed as a trimer (>200 kDa) as shown in chromatograph. The figure represents superimposed elution profiles of HEK293T cell-expressed cHA proteins overlaid with calibration standards (dotted line). (E) A schematic figure to mark the main glycans on the glycosites of $cHA_{fg}$ and $cHA_{mg}$ determined by LC-MS/MS. The general glycan symbols were followed.
Figure 5:
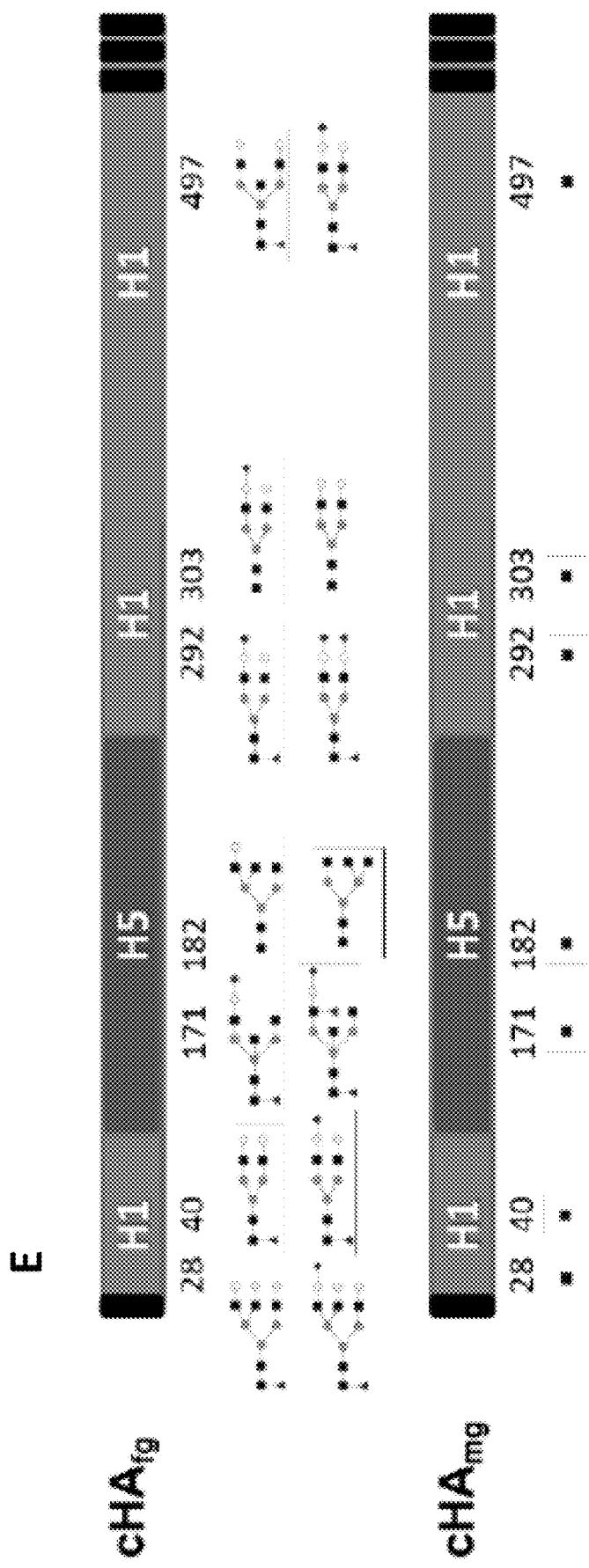
Figure 6:
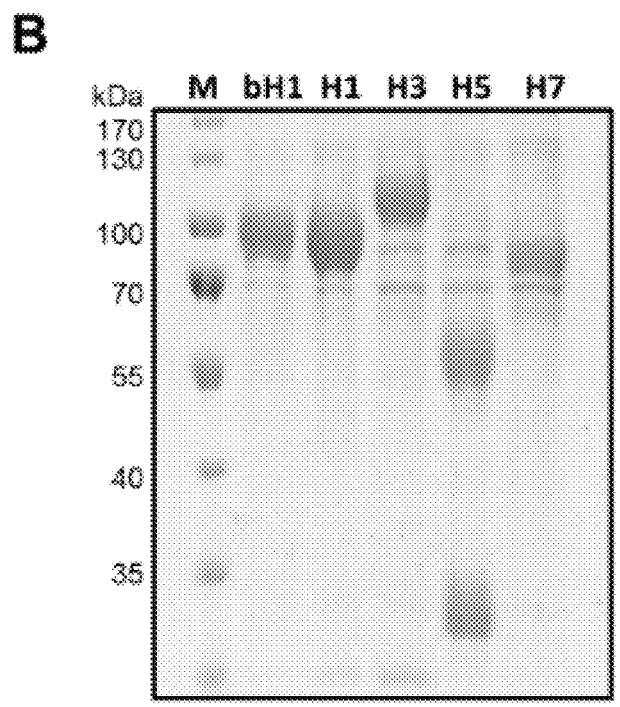
FIGS. 6(A) and (B). The constructs of secreted HA and purification. (A) The sequence encoding the ectodomain of HA was prepared in the expression vector pcDNA and transfected to HEK293T cells. The protein was engineered to contain a stabilization/trimerization signal, foldon, as well as a C-terminal $(His)_6$ tag for purification. (B) The purified HA proteins were analyzed by SDS/PAGE. M: molecular weight marker. Lane 1: H1N1 (A/Brisbane/59/2007) HA protein; lane 2: H1N1 (A/California/07/2009) HA protein; lane 3: H3N2 (Brisbane/10/2007) HA protein; lane 4: H5N1 (Vietnam/1194/2004) HA protein; lane 5: H7N9 (A/Shanghai/2/2013) HA protein.
Figure 7:
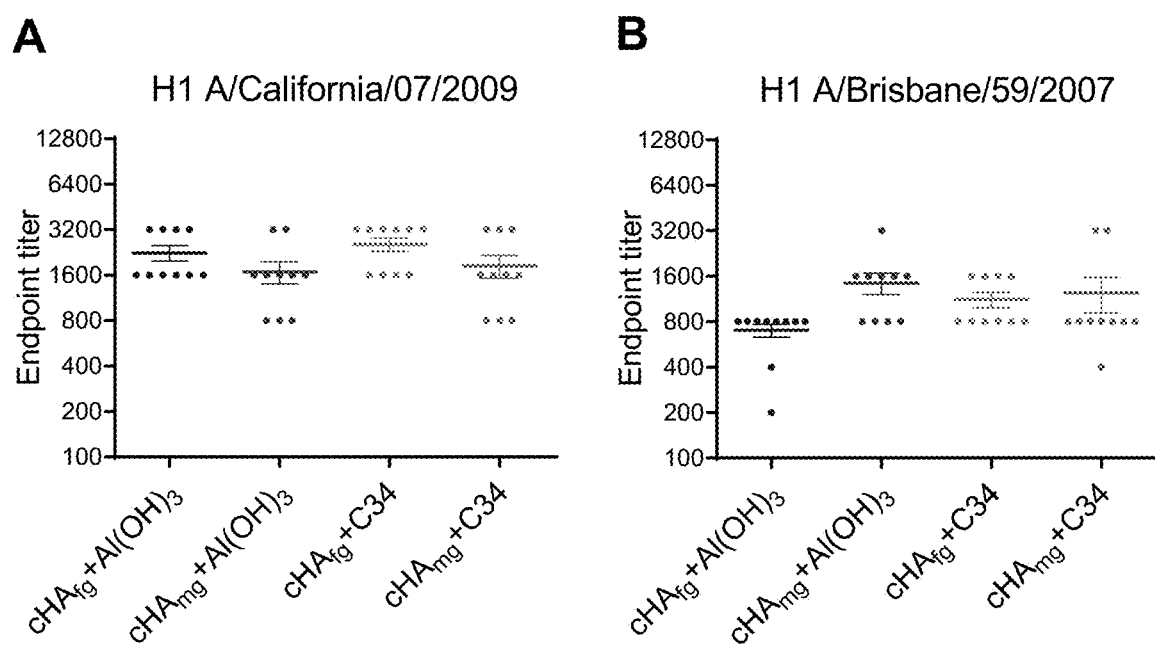
FIGS. 7(A) to (F). HA binding activities of antisera from mice vaccinated with $cHA_{fg}$ and $cHA_{mg}$. BALB/c mice (n=10 per group) were immunized at two-week intervals with $cHA_{fg}$ or $cHA_{mg}$ adjuvanted with $Al(OH)_3$ or C34. The antibody titers from the mice vaccinated with $Al(OH)_3$-adjuvanted $cHA_{fg}$ and $cHA_{mg}$ vs. C34-adjuvanted $cHA_{fg}$ and $cHA_{mg}$ were measured on day 28 by ELISA with the A/California/07/2009 H1N1 HA protein (A), A/Brisbane/59/2007 H1N1 HA protein (B), A/Brisbane/10/2007 H3N2 HA protein (C), A/Vietnam/1194/2004 H5N1 HA protein (D), A/Shanghai/2/2013 H7N9 HA protein (E) and the A/Brisbane/59/2007 (Bris/07) stem HA (#4900) protein (F) as the coating antigen. The endpoint antibody titer was defined as the highest dilution of serum to produce an absorbance 2.5 times higher than the optical absorbance (OD) produced by the negative control (pre-immune serum). Data were examined by using two-way ANOVA from Prism; differences were considered statistically significant at $P<0.01$; *$P<0.001$. Data represents the mean±SEM.
Figure 7:
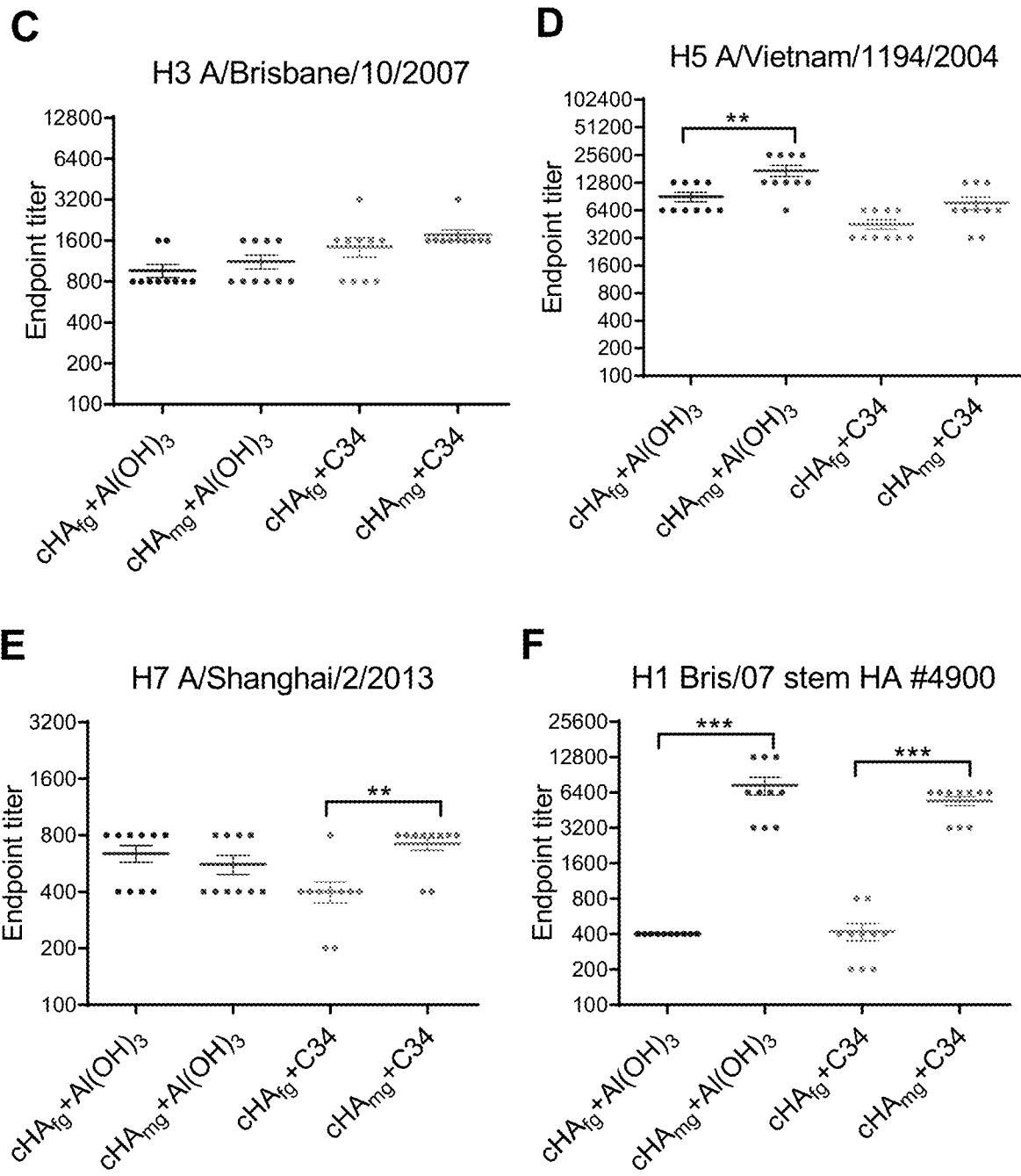
Figure 8:
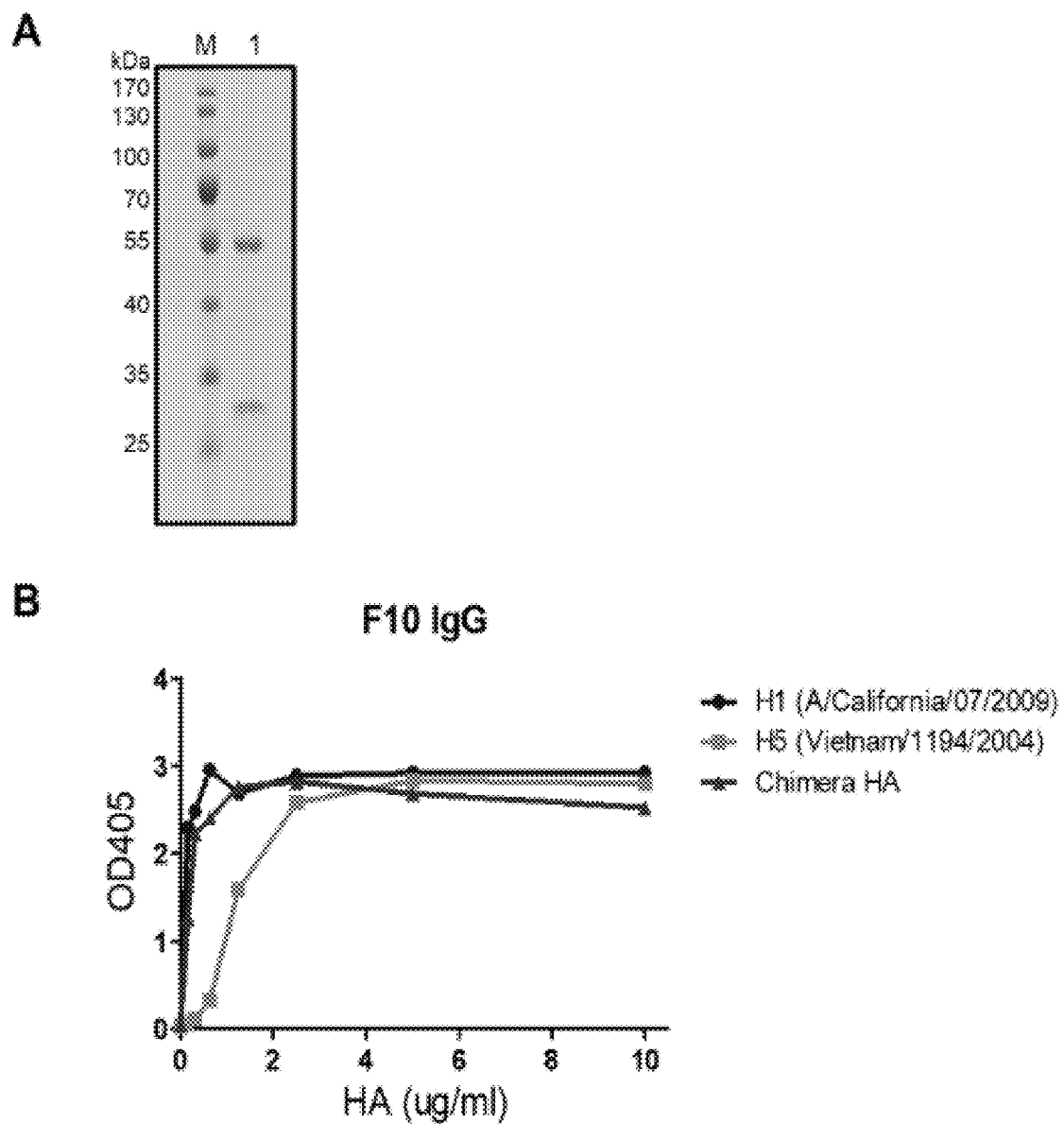
FIGS. 8(A) and (B). Binding of stalk-reactive antibodies (F10 IgG) to recombinant H1, H5 and cHAs. (A) The purified F10 was analyzed by SDS/PAGE. M: molecular weight marker. Lane 1: F10 antibody. (B) The binding affinities of F10 IgG and various HA were measured by using ELISA. The x-axis shows the concentration of various HA proteins and the y-axis shows the absorbance value at OD405 nm.

To explore the immunogenicity of the chimeric H5/1 (cHA) vaccine with different glycosylation states, monoglycosylated cHA ($cHA_{mg}$) and fully glycosylated cHA ($cHA_{fg}$) vaccine were compared (FIG. 5). It is known that Endo-H is specific for high mannose but not complex-type glycans. The HA glycoprotein expressed in HEK293S cells, which are deficient in N-acetylglucosaminyltransferase I and produce glycoproteins with high-mannose-type N-glycans, was treated with Endo-H to cleave the N-glycans to a single GlcNAc residue. To generate $cHA_{mg}$, cHA was produced from human cells (HEK293S) and the purified cHA with high-mannose glycans was treated with Endo-H to remove the outer parts of N-glycans to produce the HA with only one N-acetylglucosamine (GlcNAc) linked to the asparagine residue of each glycosite. After Endo-H treatment, the mixture was passed through gel filtration to separate Endo-H from trimeric $cHA_{mg}$. After concentration, the $cHA_{mg}$ proteins were subjected to sodium dodecyl sulfate-polyacrylamide gel electrophoresis (SDS/PAGE) and liquid chromatography-tandem mass spectrometry (LC-MS/MS) analyses to ensure purity and glycan composition (FIG. 5C). Since influenza HA exists as a trimer on the virus surface, gel filtration was performed to confirm that the $cHA_{fg}$ and $cHA_{mg}$ existed as a trimer (>200 kDa) (FIG. 5D). We also generated another fully glycosylated $cHA_{fg}$ from human cells (HEK293T) for comparison (FIG. 5B), and the cell culture yielded $cHA_{fg}$ with ~6 mg/L.

The N-linked glycosylation sites and the glycan profile of recombinant $cHA_{fg}$ and $cHA_{mg}$ were analyzed by LC-MS/MS showing seven glycosylation sites (N28, N40, N171, N182, N292, N303, and N497); the N-glycans of $cHA_{fg}$ were mostly complex type and $cHA_{mg}$ could be obtained in ~99% as a single glycoform with only GlcNAc at each of its N-glycosylation sites (FIG. 5E and Table 1).

TABLE 1

The N-linked glycan structures of cHA in fully-glycosylated and mono-glycosylated proteins analyzed by LC-MS/MS.

| | | N28 | | N40 | | N171 | | N182 |
|---|---|---|---|---|---|---|---|---|
| Glycan name | Glycan Structure | $cHA_{fg}$ | $cHA_{mg}$ | $cHA_{fg}$ | $cHA_{mg}$ | $cHA_{fg}$ | $cHA_{mg}$ | $cHA_{fg}$ |
| None | | 0% | 0% | 3% | 0% | 0% | 0% | 0% |
| Deamidated | | 0% | 0% | 0% | 0% | 0% | 0% | 0% |
| N | ■ | 0% | 100% | 0% | 100% | 0% | 95% | 0% |
| NF | ▶-■ | 0% | 0% | 0% | 0% | 6% | 0% | 0% |
| Man5 | | 3% | 0% | 3% | 0% | 0% | 0% | 0% |
| Man5NHS | | 0% | 0% | 0% | 0% | 0% | 0% | 0% |
| N-N3H5S0F0 | | 0% | 0% | 0% | 0% | 0% | 0% | 0% |

TABLE 1-continued

The N-linked glycan structures of cHA in fully-glycosylated and mono-glycosylated proteins analyzed by LC-MS/MS.

| Name | Structure | | | | | | | |
|---|---|---|---|---|---|---|---|---|
| N-N3H5S1F0 | 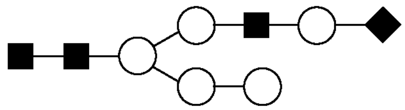 | 0% | 0% | 0% | 0% | 0% | 0% | 0% |
| N-N3H5S0F1 | 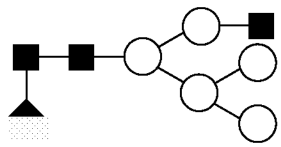 | 1% | 0% | 0% | 0% | 0% | 0% | 0% |
| N-N3H5S1F1 | 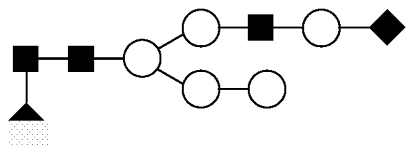 | 0% | 0% | 0% | 0% | 0% | 0% | 0% |
| N-N3H4S0F0 | 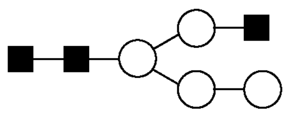 | 0% | 0% | 0% | 0% | 0% | 0% | 0% |
| NNH3NN | 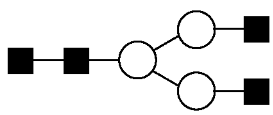 | 0% | 0% | 0% | 0% | 0% | 0% | 2% |
| H4NN | 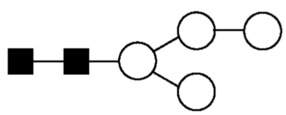 | 0% | 0% | 0% | 0% | 0% | 0% | 0% |
| NNH3NNF1-G0 | 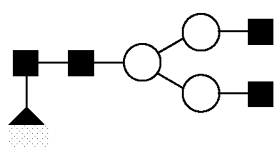 | 0% | 0% | 0% | 0% | 0% | 0% | 1% |
| Man6N1 | 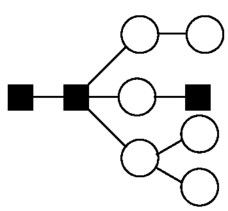 | 1% | 0% | 5% | 0% | 0% | 0% | 0% |
| BiF1-H | 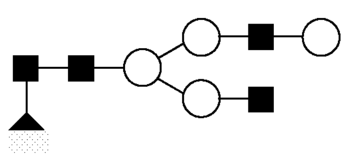 | 0% | 0% | 0% | 0% | 0% | 0% | 0% |
| BiS1 | 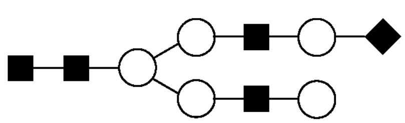 | 0% | 0% | 0% | 0% | 0% | 0% | 0% |
| BiS1-H | 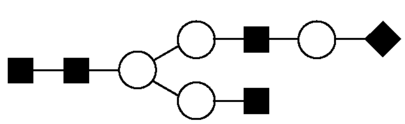 | 0% | 0% | 0% | 0% | 0% | 0% | 10% |

TABLE 1-continued

The N-linked glycan structures of cHA in fully-glycosylated and mono-glycosylated proteins analyzed by LC-MS/MS.

| Name | Structure | | | | | | | |
|---|---|---|---|---|---|---|---|---|
| BiS1F1-H | 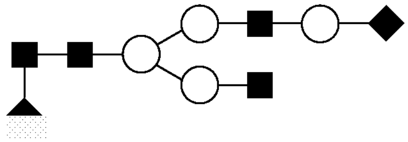 | 0% | 0% | 0% | 0% | 0% | 0% | 0% |
| BiS2 | 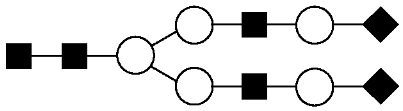 | 0% | 0% | 0% | 0% | 0% | 0% | 0% |
| BiS2-H | 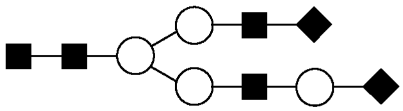 | 0% | 0% | 0% | 0% | 0% | 0% | 3% |
| BiS2N1 | 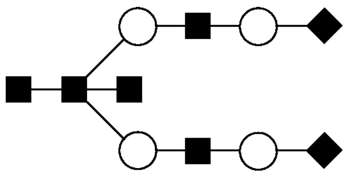 | 0% | 0% | 0% | 0% | 0% | 0% | 2% |
| Bi | 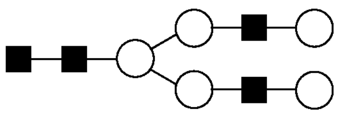 | 0% | 0% | 0% | 0% | 0% | 0% | 0% |
| N-N5H4S0F0 | 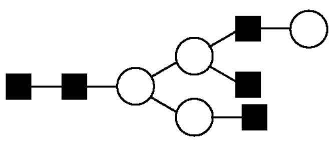 | 0% | 0% | 0% | 0% | 0% | 0% | 21% |
| N-N5H3S0F0 | 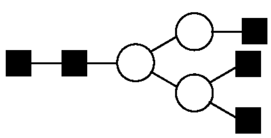 | 0% | 0% | 0% | 0% | 0% | 0% | 38% |
| N-N5H3S0F1 | 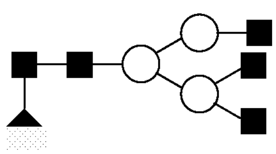 | 0% | 0% | 0% | 0% | 0% | 0% | 10% |
| BiF1 | 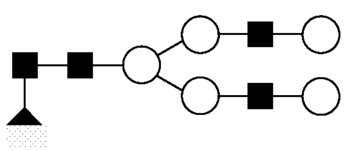 | 6% | 0% | 12% | 0% | 0% | 0% | 0% |
| Bi-H | 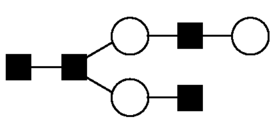 | 0% | 0% | 0% | 0% | 0% | 0% | 5% |
| BiN1 | 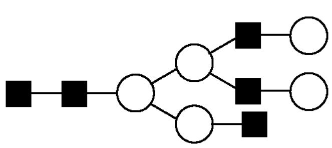 | 0% | 0% | 0% | 0% | 0% | 0% | 0% |

TABLE 1-continued

The N-linked glycan structures of cHA in fully-glycosylated and mono-glycosylated proteins analyzed by LC-MS/MS.

| | | | | | | | | |
|---|---|---|---|---|---|---|---|---|
| BiN1F1-H | | 0% | 0% | 2% | 0% | 8% | 0% | 0% |
| BiN1F2-H | | 0% | 0% | 0% | 0% | 2% | 0% | 0% |
| BiN1F1 | | 1% | 0% | 14% | 0% | 9% | 0% | 0% |
| BiS1F1 | | 3% | 0% | 25% | 0% | 6% | 0% | 0% |
| BiS2F1 | | 0% | 0% | 0% | 0% | 7% | 0% | 0% |
| N-N5H4S1F1 | | 0% | 0% | 0% | 0% | 23% | 0% | 0% |
| BiN1S1F1 | | 0% | 0% | 0% | 0% | 0% | 0% | 0% |
| BiN1S1-H | | 0% | 0% | 0% | 0% | 0% | 0% | 2% |
| N-N5H4S1F2 | | 0% | 0% | 0% | 0% | 16% | 0% | 0% |

TABLE 1-continued

The N-linked glycan structures of cHA in fully-glycosylated and mono-glycosylated proteins analyzed by LC-MS/MS.

| | | | | | | | | |
|---|---|---|---|---|---|---|---|---|
| BiN1S1F1 | | 0% | 0% | 1% | 0% | 6% | 0% | 0% |
| N-N5H4S2F1 | | 0% | 0% | 0% | 0% | 15% | 0% | 0% |
| TriF1 | | 43% | 0% | 2% | 0% | 0% | 0% | 0% |
| TriS1F1 | | 38% | 0% | 11% | 0% | 0% | 0% | 0% |
| TriN1F1 | | 3% | 0% | 0% | 0% | 0% | 0% | 0% |
| BiF1N1S2 | | 0% | 0% | 0% | 0% | 0% | 0% | 0% |
| TriS2F1 | | 0% | 0% | 0% | 0% | 0% | 0% | 0% |

TABLE 1-continued

The N-linked glycan structures of cHA in fully-glycosylated and mono-glycosylated proteins analyzed by LC-MS/MS.

| Glycan name | N182 cHA$_{mg}$ | N292 cHA$_{fg}$ | N292 cHA$_{mg}$ | N303 cHA$_{fg}$ | N303 cHA$_{mg}$ | N497 cHA$_{fg}$ | N497 cHA$_{mg}$ |
|---|---|---|---|---|---|---|---|
| TetraF1 | 0% | 0% | 2% | 0% | 0% | 0% | 0% |
| TetraS1F1 | 1% | 0% | 7% | 0% | 0% | 0% | 0% |
| TetraS2F1 | 0% | 0% | 11% | 0% | 0% | 0% | 0% |
| TetraH1S2 | 0% | 0% | 0% | 0% | 2% | 0% | 0% |
| Others | 0% | 0% | 2% | 0% | 0% | 5% | 6% |
| None | 0% | 0% | 0% | 0% | 1% | 0% | 0% |
| Deamidated | 0% | 0% | 0% | 0% | 0% | 7% | 0% |
| N | 100% | 0% | 100% | 1% | 99% | 0% | 100% |
| NF | 0% | 2% | 0% | 0% | 0% | 3% | 0% |
| Man5 | 0% | 0% | 0% | 6% | 0% | 0% | 0% |
| Man5NHS | 0% | 0% | 0% | 6% | 0% | 0% | 0% |
| N-N3H5S0F0 | 0% | 0% | 0% | 10% | 0% | 0% | 0% |
| N-N3H5S1F0 | 0% | 0% | 0% | 10% | 0% | 0% | 0% |
| N-N3H5S0F1 | 0% | 0% | 0% | 0% | 0% | 0% | 0% |
| N-N3H5S1F1 | 0% | 0% | 0% | 3% | 0% | 0% | 0% |
| N-N3H4S0F0 | 0% | 0% | 0% | 2% | 0% | 0% | 0% |
| NNH3NN | 0% | 0% | 0% | 0% | 0% | 0% | 0% |
| H4NN | 0% | 0% | 0% | 1% | 0% | 0% | 0% |
| NNH3NNF1-G0 | 0% | 0% | 0% | 0% | 0% | 0% | 0% |
| Man6N1 | 0% | 0% | 0% | 9% | 0% | 0% | 0% |
| BiF1-H | 0% | 2% | 0% | 1% | 0% | 2% | 0% |
| BiS1 | 0% | 0% | 0% | 13% | 0% | 0% | 0% |
| BiS1-H | 0% | 0% | 0% | 0% | 0% | 0% | 0% |
| BIS1F1-H | 0% | 1% | 0% | 0% | 0% | 0% | 0% |

TABLE 1-continued

The N-linked glycan structures of cHA in fully-glycosylated and mono-glycosylated proteins analyzed by LC-MS/MS.

| | | | | | | | |
|---|---|---|---|---|---|---|---|
| BiS2 | 0% | 0% | 0% | 1% | 0% | 0% | 0% |
| BiS2-H | 0% | 0% | 0% | 0% | 0% | 0% | 0% |
| BiS2N1 | 0% | 0% | 0% | 0% | 0% | 0% | 0% |
| Bi | 0% | 0% | 0% | 13% | 0% | 0% | 0% |
| N-N5H4S0F0 | 0% | 0% | 0% | 0% | 0% | 0% | 0% |
| N-N5H3S0F0 | 0% | 0% | 0% | 0% | 0% | 0% | 0% |
| N-N5H3S0F1 | 0% | 0% | 0% | 0% | 0% | 0% | 0% |
| BiF1 | 0% | 7% | 0% | 8% | 0% | 11% | 0% |
| Bi-H | 0% | 0% | 0% | 0% | 0% | 0% | 0% |
| BiN1 | 0% | 0% | 0% | 1% | 0% | 0% | 0% |
| BiN1F1-H | 0% | 1% | 0% | 3% | 0% | 7% | 0% |
| BiN1F2-H | 0% | 0% | 0% | 0% | 0% | 0% | 0% |
| BiN1F1 | 0% | 9% | 0% | 0% | 0% | 31% | 0% |
| BiS1F1 | 0% | 34% | 0% | 9% | 0% | 38% | 0% |
| BiS2F1 | 0% | 21% | 0% | 0% | 0% | 0% | 0% |
| N-N5H4S1F1 | 0% | 0% | 0% | 0% | 0% | 0% | 0% |
| BiN1S1F1 | 0% | 10% | 0% | 0% | 0% | 0% | 0% |
| BiN1S1-H | 0% | 0% | 0% | 0% | 0% | 0% | 0% |
| N-N5H4S1F2 | 0% | 0% | 0% | 0% | 0% | 0% | 0% |
| BiN1S1F1 | 0% | 0% | 0% | 0% | 0% | 0% | 0% |
| N-N5H4S2F1 | 0% | 0% | 0% | 0% | 0% | 0% | 0% |
| TriF1 | 0% | 0% | 0% | 0% | 0% | 0% | 0% |
| TriS1F1 | 0% | 3% | 0% | 0% | 0% | 1% | 0% |
| TriN1F1 | 0% | 0% | 0% | 0% | 0% | 0% | 0% |
| BiF1N1S2 | 0% | 1% | 0% | 0% | 0% | 0% | 0% |
| TriS2F1 | 0% | 4% | 0% | 0% | 0% | 0% | 0% |
| TetraF1 | 0% | 0% | 0% | 0% | 0% | 0% | 0% |
| TetraS1F1 | 0% | 0% | 0% | 0% | 0% | 0% | 0% |
| TetraS2F1 | 0% | 0% | 0% | 0% | 0% | 0% | 0% |
| TetraH1S2 | 0% | 0% | 0% | 0% | 0% | 0% | 0% |
| Others | 0% | 5% | 0% | 3% | 0% | 0% | 0% |

Example 3 Cross-Reactivity of Antisera from Mice Immunized with Fully Glycosylated Chimeric 115/1 (cHA$_{fg}$) and Monoglycosylated Chimeric 115/1 (cHA$_{mg}$)

To evaluate the binding activity of antibody elicited by cHA constructs, BALB/c mice were immunized intramuscularly with 20 μg of cHA$_{fg}$ or cHA$_{mg}$ protein adjuvanted with $Al(OH)_3$ or C34, an analog of ax-galactosylceramide (ax-GalCer). The mice were immunized at weeks 0, 2, and 4, and HA-induced serum was obtained on days 28 and 42 and measured using enzyme-linked immunosorbent assay (ELISA) with various recombinant HAs (FIG. 6). Comparing to the maximum dilution of antisera after two immunizations, three immunizations indeed produced antiserum with higher titers of HA-specific antibodies (FIG. 1D-I and FIG. 7), and vaccination with $cHA_{mg}$ induced better antibody response compared to $cHA_{fg}$ (FIGS. 1D, E, and G). In addition, the antiserum from $cHA_{mg}$ showed slightly better binding to H3 and H7 HA proteins (FIGS. 1F and H), and no significant differences were observed between $Al(OH)_3$ and C34 adjuvants. These data indicate that the cHA vaccine could elicit cross-reactive antibodies recognizing the HA from H1N1, H3N2, H5N1, as well as H7N9 strains.

F10 is a broadly neutralizing JgG antibody known to target the stem region of HA, which is highly conserved among various subtypes of influenza viruses. To compare the binding of F10 to recombinant H1, H5, and cHA, the binding avidities of F10 to various HAs were measured, and the results showed that F10 could bind H1, H5, and cHA proteins (FIG. 8). To investigate if F10-like antibodies were elicited by cHA vaccination, the binding of cHA-induced serum to HA stem no. 4900 was measured by using ELISA. The results showed that the $cHA_{mg}$ vaccine can induce higher stem-specific antibody titer than $cHA_{fg}$ (FIG. 1I and FIG. 7F), and better results were observed with C34-adjuvanted cHA vaccine (FIG. 11), which in-duced more stem-specific antibodies.

Example 4 Vaccination of Mice with $cHA_{mg}$ and Adjuvant C34 Elicits Strong $CD4^+$ and $CD8^+$ T-Cell Responses and Antibody-Dependent Effector Functions, and Neutralizing Activities Against H1, H3, H5 Viruses as Well as their Subtypes Besides antibody-mediated neutralization, Fc-mediated effector functions also play an important role in protection against influenza infection. We therefore examined whether the antibodies would induce Fc receptor-mediated immune response. The mouse-adapted ADCC assay was performed using Jurkat effector cells expressing FcγRIII to evaluate the ADCC activities of the sera from $cHA_{fg}$- and $cHA_{mg}$-immunized mice (FIG. 2). As expected, the serum from $cHA_{f}g$- or $cHA_{mg}$-vaccinated mice induced comparable levels of ADCC activities against H5N1 NIBRG14 (A/Vietnam/1194/2004), NIBRG23 (A/Turkey/1/2005), RG5 (A/Anhui/1/2005), or RG2 (A/Indonesia/5/2005) viruses. Interestingly, better ADCC activities were observed in the $cHA_{mg}$ group adjuvanted with $Al(OH)_3$ (FIG. 2B), and similar results were observed in experiments against H1N1 A/California/07/2009, A/Brisbane/59/2007, A/Solomon Islands/3/2006, A/New Caledonia/20/1999 (FIG. 2A), H3N2 A/Wisconsin/67/2005, and A/Victoria/361/2011 viruses (FIG. 2C).

To evaluate the role of antigen-specific cytokine-secreting cells in cHA-immunized mice, the splenocytes were collected after two and three immunizations and the IFN-γ, IL-4, and granzyme B (GzB)-secreting cells were estimated by enzyme-linked immune absorbent spot (ELISpot) assays with specific peptides from HA for stimulation. As shown in FIG. 3, the $cHA_{fg}$ and $cHA_{mg}$ vaccines adjuvanted with Al(OH)$_3$ produced similar levels of cytokine-secreting cells. However, more CD4$^+$/IFN-γ' Th1 cells (FIG. 3A), CD4$^+$/IL-4$^+$ Th2 (FIG. 3B), and CD8$^+$ GzB-secreting cells (FIG. 3C) were elicited in cHA$_{mg}$ vaccination adjuvanted with C34 than with Al(OH)$_3$. These results confirmed that cHA$_{mg}$ adjuvanted with C34 could stimulate more CD4$^+$ T helper response and stronger CD8$^+$ cytotoxicity effects compared to cHA$_{fg}$.

Figure 9:
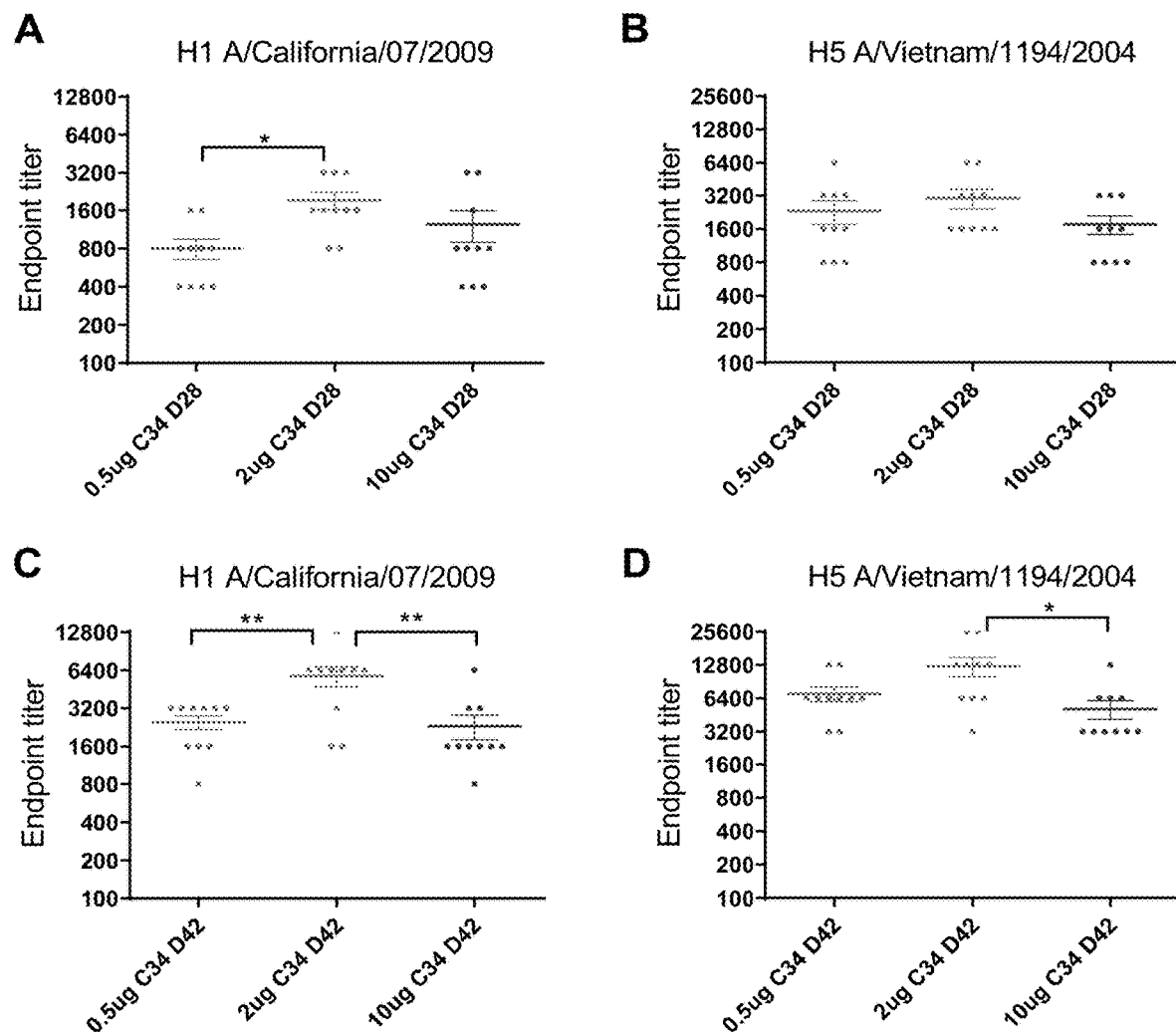
FIGS. 9(A) to (D). Dose-dependent effects of C34 on antibody titers. BALB/c mice (n=10 per group) were injected at two-week intervals with 20 μg cHA adjuvanted with 0.5 μg, 2 μg or 10 μg of C34. Mice sera were collected two weeks after the second (D28) and third (D42) immunizations. The antibodies titers were measured by using ELISA with HA proteins of H1N1 A/California/07/2009 (A and C) and H5N1 Vietnam/1194/2004 (B and D). The P value of antibody titers was calculated by using two-way ANOVA from Prism; differences were considered statistically significant at *P<0.05; **P<0.01. Data represents the mean±SEM.
Figure 10:
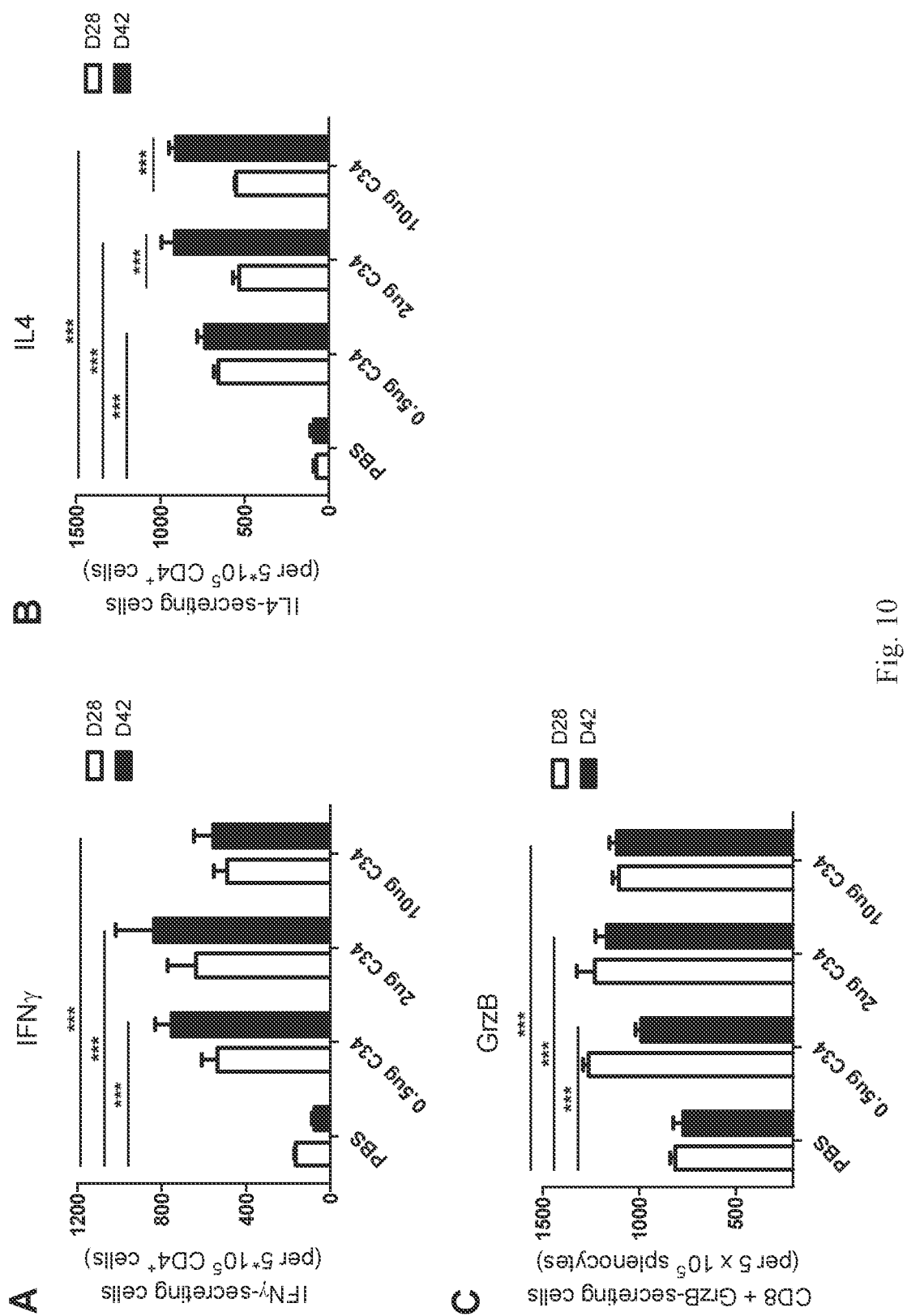
FIGS. 10(A) to (C). Dose-dependent effects of C34 on antigen-specific cytokine-secreting cells. BALB/c mice (n=5 per group) were injected at two-week intervals with 20 µg of purified cHA adjuvanted with three different doses of C34 at 0.5, 2 and 10 µg. The splenocytes of cHA immunized mice were obtained after the second (D28) and third (D42) immunizations. (A) IFN-γ and (B) TL4-secreting cells were assessed by Elispot analysis. (C) The number of granzyme B producing $CD8^+$ T cell in splenocytes was determined by Elispot analysis using specific peptides. ***P<0.001. The P value were calculated with Prism software using two-way ANOVAs.

To evaluate the dose dependence of C34 on antibody titers and cell-mediated immunity, mice were immunized intramuscularly with cHA$_{fg}$ adjuvanted with three different doses of C34 at 0.5, 2, and 10 μg. The result indicated that cHA$_{fg}$ adjuvanted with 2 μg of C34 induced higher titers than with 0.5 and 10 μg of C34 after two or three immunizations (FIG. 9). In addition, the cHA$_{fg}$ vaccine adjuvanted with 2 μg of C34 induced more IFN-γ than with 0.5 and 10 μg of C34 (FIG. 10A) and 2 and 10 μg of C34 induced more IL-4 than with 0.5 μg of C34 after three immunizations (FIG. 10B). On the other hand, there were no differences with regard to the increase in CD8$^+$ GzB-secreting cells when the cHA$_{fg}$ vaccine was adjuvanted with 0.5, 2, or 10 μg of C34 after two and three immunizations (FIG. 10C). Based on these observations, 2 μg of C34 were used throughout the experiments.

Figure 3:
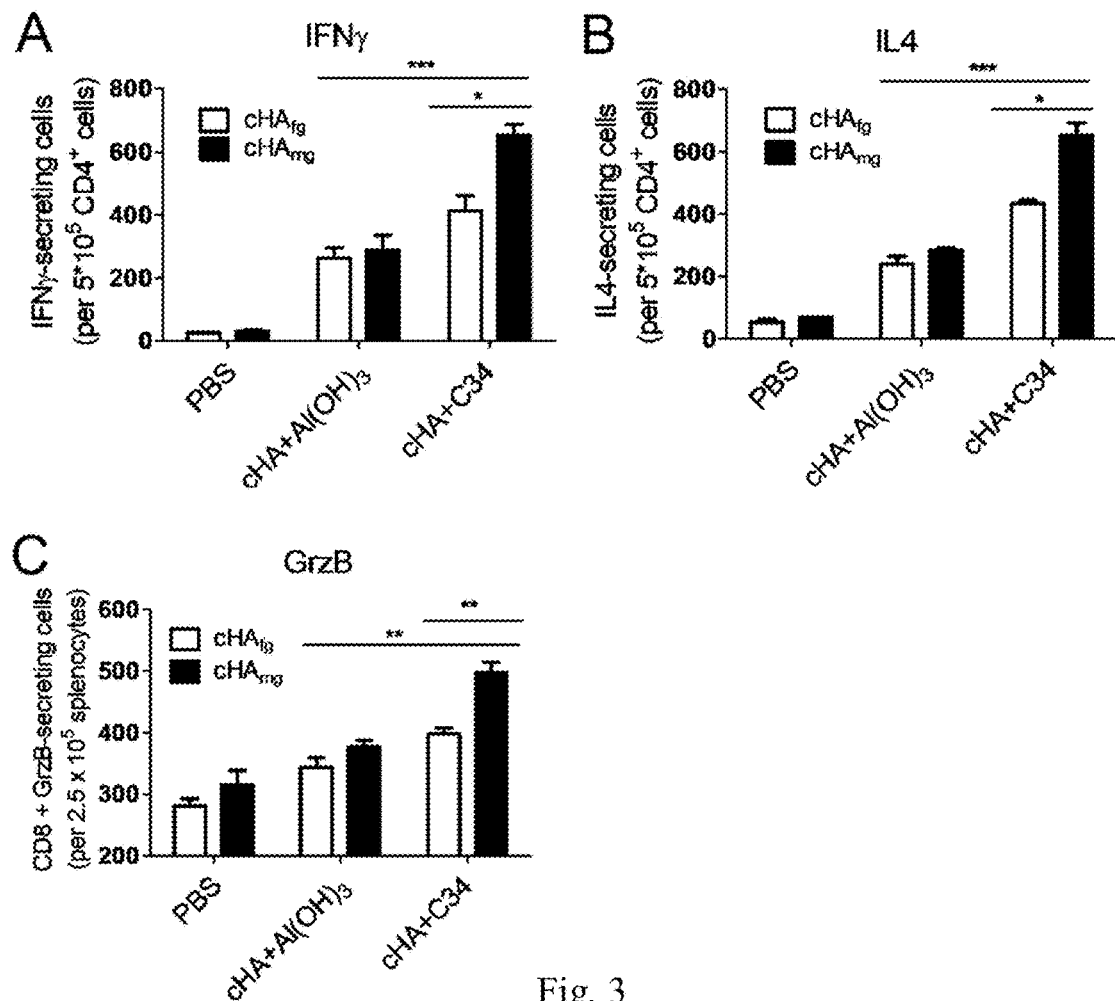
FIGS. 3(A) to (E). More $CD4^+$ and $CD8^+$ T-cell responses and broadly neutralizing antibodies were elicited to give broader cross-protection by $cHA_{mg}$ with adjuvant C34. BALB/c mice were immunized with $cHA_{fg}$ and $cHA_{mg}$ with adjuvant $Al(OH)_3$ or C34; cells from spleens of immunized mice were obtained after three immunizations and the IFN-7 (A), IL-4 (B) and GzB (C)-secreting cells were determined by ELISpot assay using specific peptides. The number of spot-forming cells (SFCs) is expressed as mean±SEM. The neutralization activities of antisera from $cHA_{fg}$ and $cHA_{mg}$ vaccinated mice were assayed against (D) H1N1 virus, and (E) H5N1 virus. Data are presented as mean±SEM. Results were calculated with Prism software using Student's t test and two-way ANOVA; significant differences were marked as *$P<0.05$; $P<0.01$; *$P<0.001$.
Figure 3:
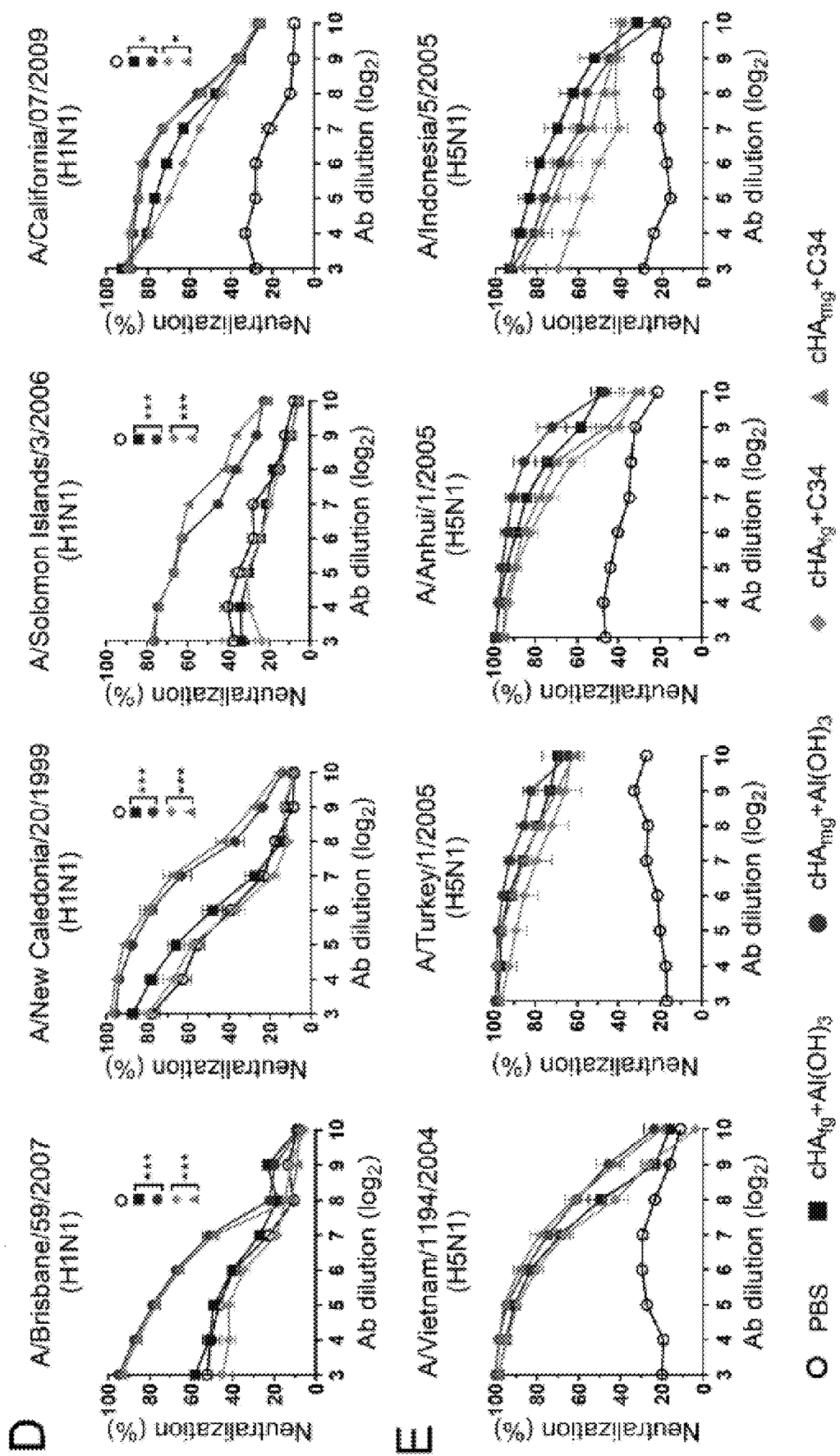

The neutralizing activities of cHA-induced antisera were further investigated. The antisera from cHA$_{mg}$ vaccination were shown to have better neutralization activities against the homologous viruses H1N1 A/California/07/2009 (FIG. 3D) and heterologous H5N1 NIBRG14 (A/Vietnam/1194/2004), NIBRG23 (A/Turkey/1/2005), RG5 (A/Anhui/1/2005), or RG2 (A/Indonesia/5/2005) (FIG. 3E). In addition, the antisera from mice vaccinated with cHA$_{mg}$ exhibit significant neutralizing activities against heterologous viruses H1N1 A/Brisbane/59/2007, A/New Caledonia/20/1999, and A/Solomon Islands/3/2006 (FIG. 3D). The antisera from cHA-immunized mice were clearly able to block the infection of H1N1 and H5N1 viruses, and the neutralizing activity of cHA$_{mg}$ was in general better than cHA$_{fg}$, particularly against the heterologous viruses.

Figure 4:
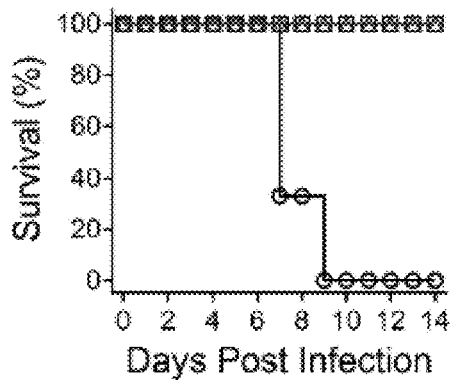
FIGS. 4(A) to (F). Cross-protective efficacy in mice challenged with lethal doses of H1N1 and H5N1 viruses. BALB/c mice were immunized with three doses of $cHA_{fg}$ and $cHA_{mg}$ with adjuvant $Al(OH)_3$ or C34 at 2-week intervals. The immunized mice were challenged with H1N1 A/California/07/2009 (A), H1N1 A/New Caledonia/1999 (B), H1N1 A/WSN/1933 (C) H1N1 A/Solomon Islands/03/2006 (D) H5N1 A/Vietnam/1194/2004/NIBRG14 (E), or H5N1 A/Turkey/1/2005/NIBRG23 (F), and the efficacy was evaluated by recording the survival rate for 14 days after infection. **$P<0.01$. Significant differences in survival rate were analyzed by log-rank (Mantel-Cox) test.
Figure 4:
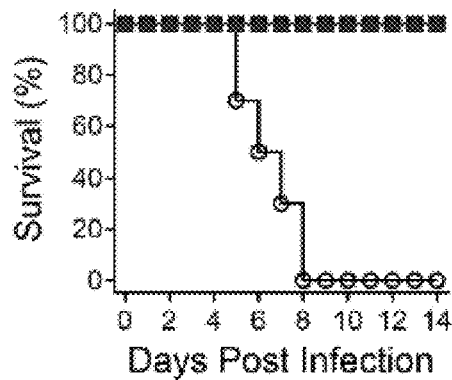
Figure 4:
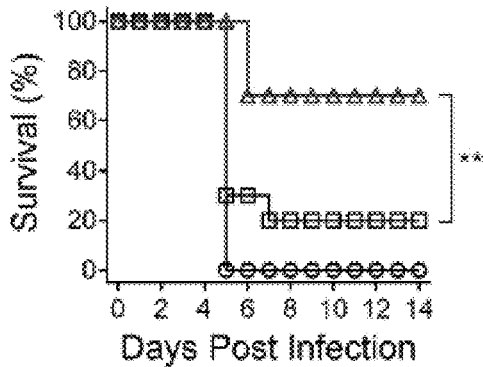
Figure 4:
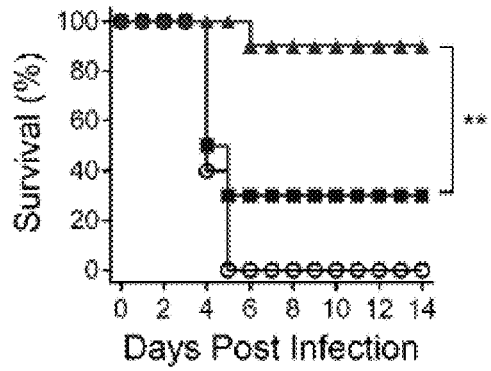
Figure 4:
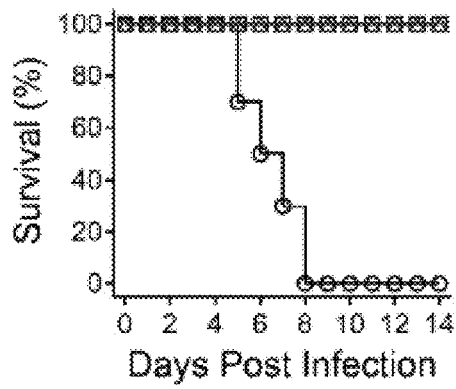
Figure 4:
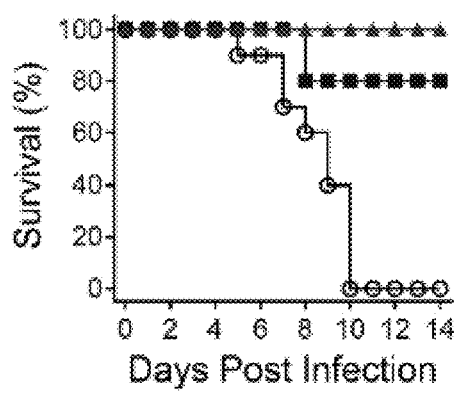
Figure 4:
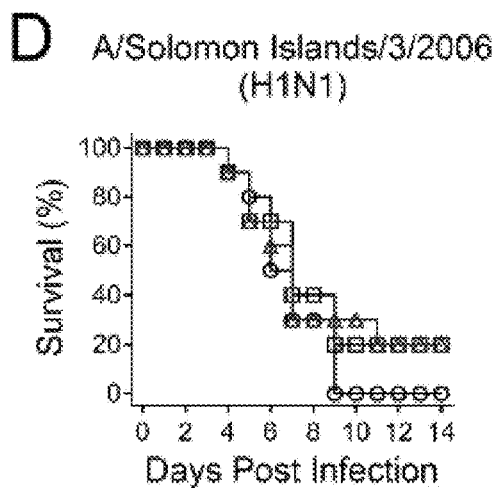
Figure 4:
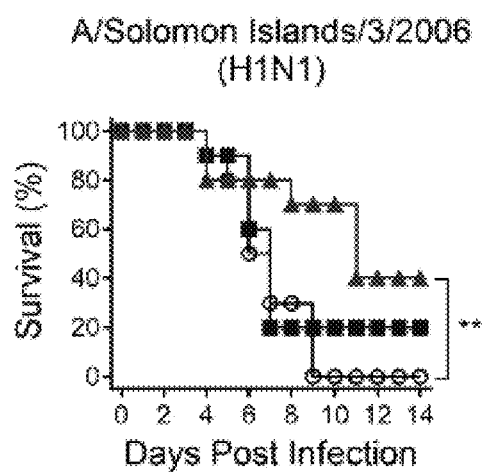
Figure 4:
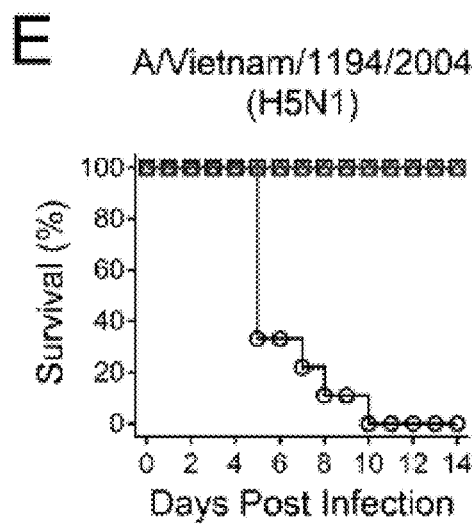
Figure 4:
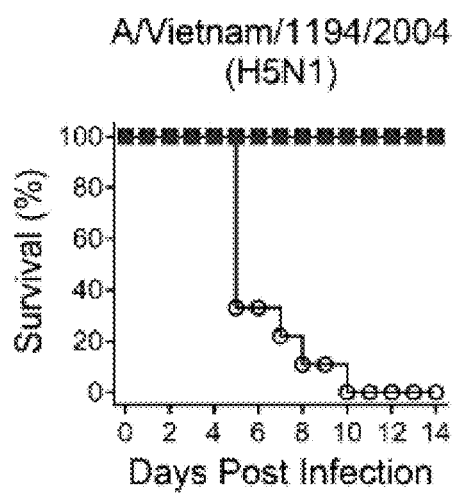
Figure 4:
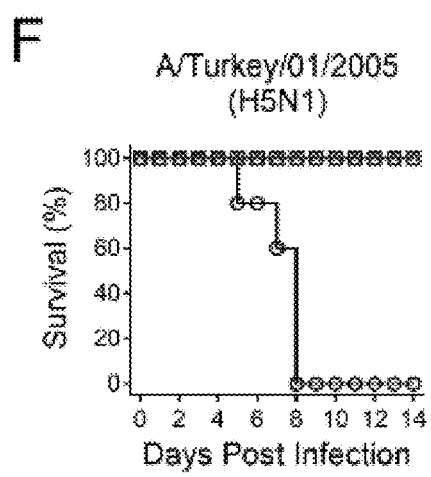
Figure 4:
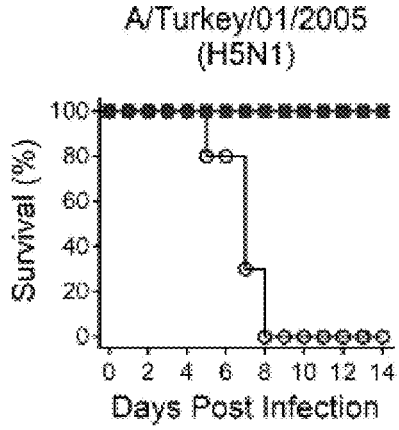
Figure 11:
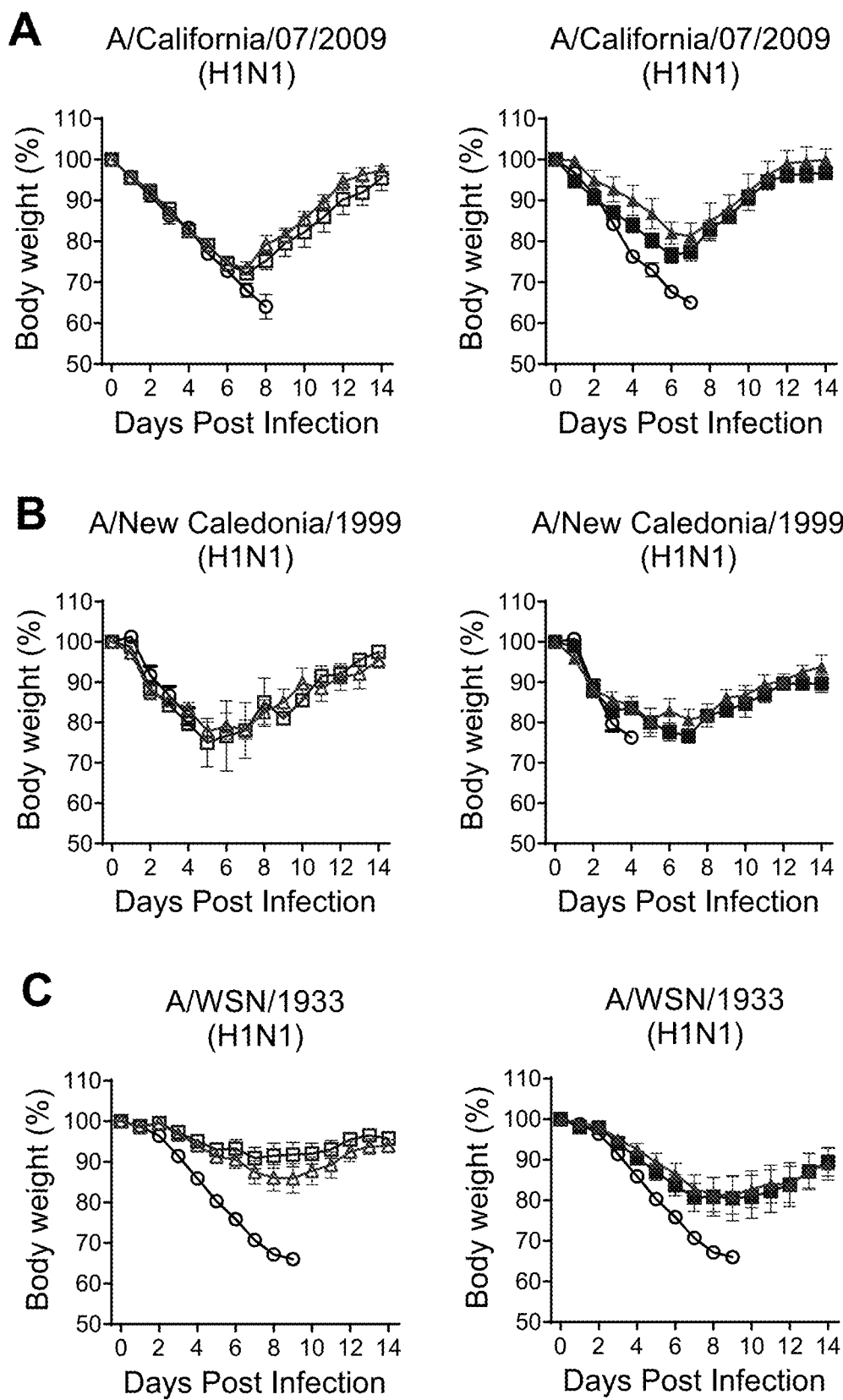
FIGS. 11(A) to (F). The body weight of $cHA_{fg}$ or $cHA_{mg}$ vaccinated mice challenged by H1N1 and H5N1 viruses at lethal dose. Body-weight changes of immunized mice challenged with H1N1 A/California/07/2009 (A), H1N1 A/New Caledonia/1999 (B), H1N1 A/WSN/1933 (C), H1N1 A/Solomon Islands/03/2006 (D), H5N1 A/Vietnam/1194/2004 (E), or H5N1 A/Turkey/1/2005 (F) viruse were monitored for 14 days after infection. Body-weight change is presented as mean±SEM.
Figure 11:
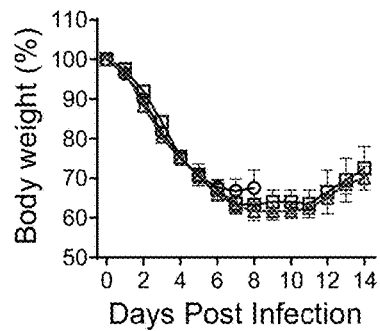
Figure 11:
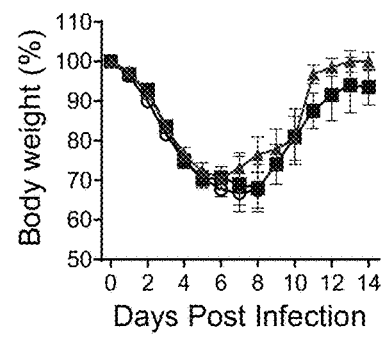
Figure 11:
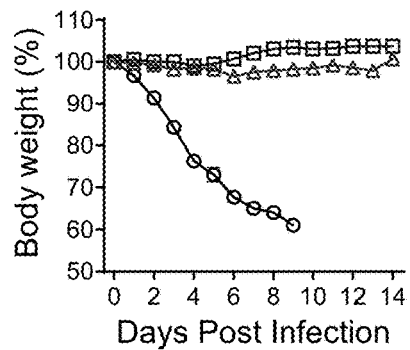
Figure 11:
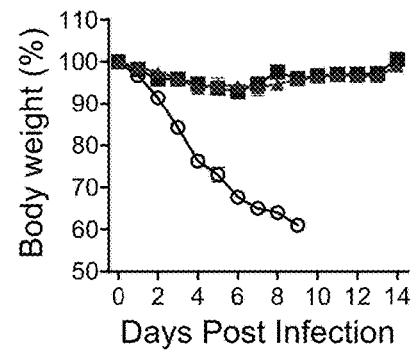
Figure 11:
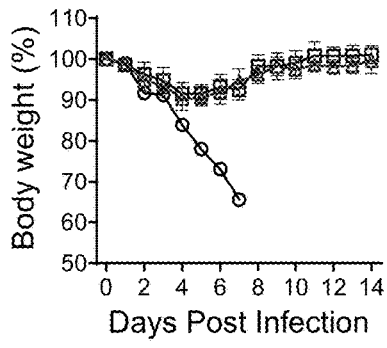
Figure 11:
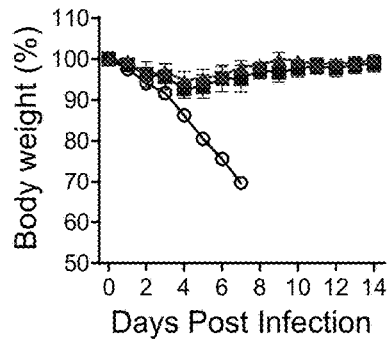

Example 5 Vaccination of Mice with cHA$_{mg}$/C34 Provides Cross-Protection Against H1N1 and H5N1 as Well as their Subtypes in the Challenge Study In order to assess whether cHA$_{mg}$ vaccination provides broadly cross-protective immunity against various H1N1 and H5N1 viruses, the vaccinated mice were challenged by intranasal inoculation with lethal doses of multiple H1N1 and H5N1 viruses, and the efficacy of vaccine protection was evaluated for 14 d by recording the survival rate and body weight change (FIG. 4 and FIG. 11). For the mice challenged with H1N1 A/California/07/2009 viruses, all cHA vaccines offered 100% protection (FIG. 4A). In addition, the mice immunized with C34-adjuvanted cHA$_{mg}$ showed minimal amounts of weight loss compared with cHA$_{fg}$ (FIG. 11A). The mice immunized with C34-adjuvanted cHA$_{fg}$ only gave 30% protection against A/New Caledonia/1999 challenges; however, the cHA$_{mg}$ vaccine adjuvanted with C34 offered 90% protection against cross-strain A/New Caledonia/1999 viruses, and similar 1 results were observed in Al(OH)$_3$-adjuvanted cHA vaccination (FIG. 4B). For the mice challenged with cross-strain A/WSN/1933 viruses, all mice immunized with Al(OH)$_3$-adjuvanted cHA survived; however, the mice immunized with C34-adjuvanted cHA$_{fg}$ only gave 80% protection (FIG. 4C). The lethal challenges were also performed with A/Solomon Islands/03/2006. All mice immunized with Al(OH)$_3$-adjuvanted cHA showed lower protection; however, the mice immunized with C34-adjuvanted cHA$_{mg}$ showed better protection against cross-strain A/Solomon Islands/03/2006 viruses (FIG. 4D). For the mice challenged with H5N1 NIBRG14 (A/Vietnam/1194/2004) and NIBRG23 (A/Turkey/1/2005), all immunized mice survived (FIGS. 4E and F). The body weight changes after viral challenges were also evaluated (FIG. 11). The data showed that cHA was effective in eliciting a significant protective immunity against various H1N1 and H5N1 viruses, and cHA$_{mg}$ provides a broader cross-protection ability compared to cHA$_{fg}$.

Development of universal influenza vaccine to provide protection against multiple strains and subtypes of influenza viruses is of current interest, and the epitopes used for universal vaccine development include the highly conserved ectodomain of M2 containing 24 nonglycosylated amino acids, the nucleoprotein NP, and the various HA constructs which have been shown to induce higher titers of broadly neutralizing antibodies to target the HA-stem region or block viral entry. For example, a soluble trimeric HA (mini-HA) vaccine with realigned stem subunit was shown to completely protect mice from lethal challenge by heterologous and heterosubtypic viruses, and a chimeric HA vaccination with DNA prime-protein boost and exposure to the same stem region and divergent exotic head domains was shown to elicit broadly protective stem-specific antibodies. However, the result showed that CD8$^+$ T cells did not play a key role in the cross-protective activities. Although DNA vaccines are promising, they are still in the early stage of development. In this study, the cHA constructs that express the consensus H5 of globular head and the consensus H1 of stem region were designed to mimic the real status of influenza virus transmitting from avian virus to human. Both fully glycosylated cHA$_{fg}$ and monoglycosylated cHA$_{mg}$ were prepared for comparison, and the result showed that the cHA$_{mg}$ vaccine elicited higher titers of cross-reactive antibodies against H1, H3, H5, and H7 subtypes (FIG. 1D-H) through CD4$^+$ and CD8$^+$ T cell responses (FIG. 3A-C).

Figure 2:
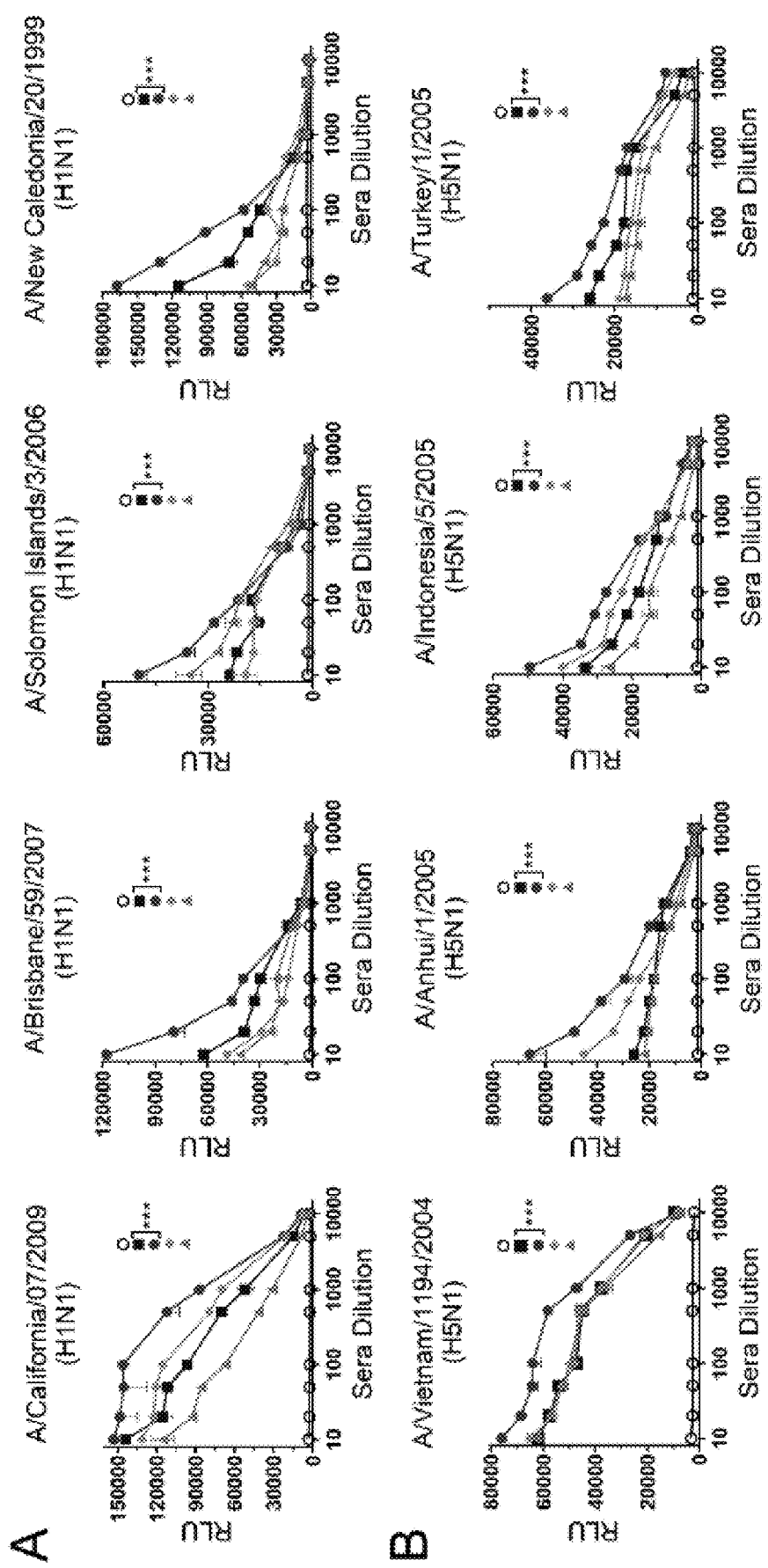
FIGS. 2(A) to (C). ADCC reporter assay of antisera from cHA-vaccinated mice against target cells expressing the HA of H1N1, H3N2 or H5N1 and subtypes. The antisera collected from mice immunized with $cHA_{fg}$ or $cHA_{mg}$ proteins adjuvanted with aluminum hydroxide or C34 were incubated with MDCK cells which were infected with (A) H1N1 virus (B) H5N1 virus, or (C) H3N2 virus for 30 min. Subsequently, the ADCC reporter assay was performed using Jurkat effector cells expressing mouse FcγRIII and the relative luminescence unit (RLU) was measured and values are mean±SEM. ***$P<0.001$. The P value was calculated with Prism software using two-way ANOVAs.
Figure 2:
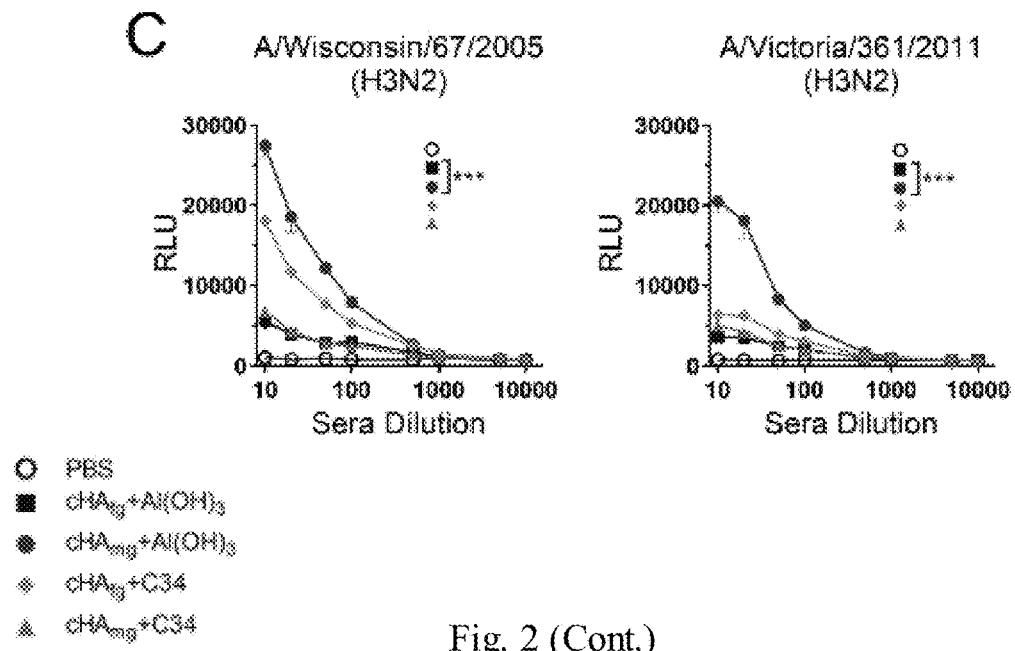

The glycosylation of HA was shown to play an important role in protein folding and stability and in modulating its biological activities, including shielding the antigenic sites from neutralizing antibodies to reduce the immunogenicity. In addition, hyperglycosylated HA was evolved to mask the antigenic sites in the highly variable head domain and the immune response was thus redirected toward the conserved stem region. In our results, the neutralization activities of the cHA$_{mg}$ antiserum were significantly superior to the cHA$_{fg}$-induced antiserum, especially against the heterologous H1N1 A/Brisbane/59/2007, A/Solomon Islands/03/2006, and A/New Caledonia/20/1999 (FIG. 3D). The broader neutralizing activities of cHA$_{mg}$ vaccine is probably due its induction of more antibody variants as reported previously. IgG is the predominant antibody present in mouse and is the major subtype of HA-specific antibodies with high avidity to the FcγRIII receptor on immune cells to induce ADCC. We showed that immunization with cHA$_{mg}$ induced higher ADCC and more stem-specific antibodies with better protection activity (FIGS. 1I and 2), consistent with the studies showing that ADCC is necessary for influenza protection in vivo. Aluminum hydroxide (Alum) was known to stimulate Th2 response and was approved by the FDA for use as vaccine adjuvant; however, its mode of action has not been well studied. The glycolipid C34 is a ligand for and presented by CD1d on dendritic cells to interact with a receptor on invariant natural killer T (iNKT) cells, leading to the stimulation of iNKT cells to produce Th1 cytokines (e.g., IFN-γ) with adjuvant effect and Th2 cytokines (e.g., IL-4)

with class-switch activity. In our results, the number of IFN-γ (Th1 cytokine), IL-4 (Th2 cytokine)-secreting cells, and the granzyme B-producing CD8⁺ T cells were significantly increased by immunization with cHA$_{mg}$ adjuvanted with C34 than with Al(OH)$_3$ (FIG. 3A-C).

In summary, development of next-generation influenza vaccines with broad-protective immune responses is of current interest, and some promising results have been reported, making the development of a universal vaccine within reach. In an effort directed toward this goal, we have successfully demonstrated in this study a proof of principle that the monoglycosylated cHA vaccine with consensus H5 head and consensus H1 stem is an effective influenza vaccine exhibiting a broad protection activity against heterologous influenza viruses, including H1, H3, H5, and H7 viruses and subtypes in the neutralizing study and H1N1, H5N1, and subtypes in the challenge study. With the success in the development of a broadly protective vaccine against different strains and subtypes of influenza A virus, we aim to use the strategy developed in this study to design a broader universal vaccine against influenza A and B viruses.

What is claimed is:

1. A chimeric influenza virus hemagglutinin (HA) polypeptide, comprising one or more stem domain sequence, each having at least 60% homology with a stem domain consensus sequence of H1 subtype HA (H1 HA) and/or H5 subtype HA (H5 HA), fused with one or more globular head domain sequence, each having at least 60% homology with a globular head domain consensus sequence of H1 subtype HA (H1 HA) or H5 subtype HA (H5 HA), wherein the chimeric influenza virus HA polypeptide comprises an amino acid sequence of SEQ ID NO: 4, SEQ ID NO: 8, or SEQ ID NO: 12.

2. The polypeptide of claim 1, wherein one or more glycosites on HA are monoglycosylated, wherein the monoglycosylated HA has only N-Acetylglucosamine (GlcNAc) on each glycosite.

3. The polypeptide of claim 1, wherein the chimeric influenza virus HA polypeptide is used as an immunogen.

4. An immunogenic composition comprising the chimeric influenza virus HA polypeptide of claim 1 and an adjuvant.

5. The immunogenic composition of claim 4, wherein the adjuvant is a glycolipid adjuvant.

6. A method of immunizing a subject against influenza virus or preventing an influenza virus disease comprising administering an effective amount of a chimeric influenza virus hemagglutinin (HA) polypeptide of claim 1 to the subject.

7. The method of claim 6, wherein the method elicits CD4$^+$ and CD8$^+$ T-cell immune responses.

8. The method of claim 6, wherein the method induces stem-specific antibodies, with higher antibody-dependent cellular cytotoxicity (ADCC), better neutralizing and stronger cross-protection activities against H1, H3, H5 and H7 strains and subtypes.

9. The method of claim 6, wherein the method enhances the vaccine efficacy with more IFN-γ, IL-4 and CD8$^+$ memory T cells produced.

10. A recombinant polynucleotide comprising a nucleic acid sequence encoding the polypeptide of claim 1 and optionally a nucleic acid sequence encoding a signal peptide.

11. The recombinant polynucleotide of claim 10, wherein the signal peptide comprises a sequence of SEQ ID NO: 13 or SEQ ID NO: 14.

12. A vector comprising the recombinant polynucleotide of claim 11.

13. A host cell comprising the vector of claim 12.

14. A method of immunizing a subject against influenza virus or preventing an influenza virus disease comprising administering an effective amount of an immunogenic composition of claim 4 to the subject.

* * * * *